(12) United States Patent
Roopenian

(10) Patent No.: US 6,992,234 B2
(45) Date of Patent: Jan. 31, 2006

(54) FCRN-BASED THERAPEUTICS FOR THE TREATMENT OF AUTO-IMMUNE DISORDERS

(75) Inventor: Derry Roopenian, Salisbury Cove, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 291 days.

(21) Appl. No.: 09/993,322

(22) Filed: Nov. 6, 2001

(65) Prior Publication Data

US 2002/0138863 A1      Sep. 26, 2002

Related U.S. Application Data

(60) Provisional application No. 60/266,649, filed on Feb. 6, 2001, provisional application No. 60/246,207, filed on Nov. 6, 2000.

(51) Int. Cl.
*G01N 33/00* (2006.01)
*A01H 67/00* (2006.01)
*C12N 15/00* (2006.01)

(52) U.S. Cl. .................. 800/3; 800/8; 800/13; 800/18; 800/21

(58) Field of Classification Search .................. 800/3, 800/8, 18, 13, 21
See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,530,101 | A | 6/1996 | Queen et al. |
| 5,585,089 | A | 12/1996 | Queen et al. |
| 5,693,761 | A | 12/1997 | Queen et al. |
| 5,877,396 | A | 3/1999 | Ravetch et al. |
| 6,096,871 | A | 8/2000 | Presta et al. |
| 6,121,022 | A | 9/2000 | Presta et al. |

OTHER PUBLICATIONS

Linder, Lab Animal May 2001;30:34-9.*
Nebert et al, Biochemical Pharmacol Feb. 1997;53:249-54.*
Mullins et al, J Clin Invest Apr. 1996;97:1557-60.*
Logan and Sharma, Clin Exp Pharmacol Physiol Dec. 1999; 26:1020-25.*
Theofilopolos and Dixon, *Adv. Immunol.* 37: 269-390 (1985).
Raghavan et al., *Immunity* 1: 303-315 (1994).
Morel et al., *Immunity* 1: 219-229 (1994).
Murphy and Roths, *Arthritis Rheum.* 22: 1188-1194 (1979).
Andrews et al., *J. Exp. Med.* 148: 1198-1215 (1978).
Simister and Mostov, *Nature* 337: 184-7 (1989).
Simister et al., *Eur. J. Immunol.* 26: 1527-31 (1996).
Ghetie et al., *Eur. J. Immunol.* 26: 690-696 (1996).
Ghetie and Ward, *Annu. Rev. Immunol.* 18: 739-66 (2000).
Brambell et al., *Nature* 203: 1352-5 (1964).
Brambell, F.W., *Lancet.* 2: 1087-93 (1966).
Capecchi, M.R., *Trends Genet.* 5: 70-76 (1989).
Israel et al., *Immunology* 89: 573-578 (1996).
Karlsson et al., *Proc. Natl. Acad. Sci. USA* 96: 2244-2249 (1999).
Israel et al., *J. of Immun.* 154: 6246-6251 (1995).
Zhiya Yu et al., "Mechanism of Intravenous Immune Globulin Therapy in Antibody-Mediated Autoimmune Diseases," New England Journal of Medicine 340(3):227-228 (1999).
Amos Etzioni et al., "High Dose Intravenous Gammaglobulins in Autoimmune Disorders: Mode of Action and Therapeutic Uses," Autoimmunity 3:307-315 (1989).
Robert A. Good et al., "Historic Aspects of Intravenous Immunoglobulin Therapy," Cancer 68:1416-1419 (1991).
Ghetie et al., "Increasing the serum persistence of an IgG fragment by random mutagenesis," Nature Biotechnology 15:637:640 (1997).

* cited by examiner

*Primary Examiner*—Q. Janice Li
(74) *Attorney, Agent, or Firm*—Fish & Neave IP Group Ropes & Gray LLP

(57)         ABSTRACT

Disclosed is a transgenic knockout mouse whose genome comprises a homozygous disruption in its endogenous FcRn gene. The homozygous FcRn disruption prevents the expression of a functional FcRn protein, resulting in a transgenic knockout mouse in which exogenously administered IgG1 exhibits a substantially shorter half-life, as compared to the half-life of exogenously administered IgG1 in a wild-type mouse. The transgenic knockout mouse with a homozygous FcRn disruption is also unable to absorb maternal IgG in the prenatal or neonatal stage of development. Also disclosed is a transgenic knockout mouse comprising a homozygous FcRn disruption and a human FcRn transgenic. The transgenic addition of human FcRn results in a substantial increase in the half-life of exogenously administered human IgG1. Methods of using the transgenic knockout mouse, and cells derived from them, are also disclosed.

11 Claims, 8 Drawing Sheets

FCRN-BASED THERAPEUTICS FOR THE TREATMENT OF AUTO-IMMUNE DISORDERS

RELATED APPLICATIONS

This application claims the benefit of the filing date of U.S. application Ser. Nos. 60/266,649, filed on Feb. 6, 2001 and 60/246,207, filed on Nov. 6, 2000. The entire teachings of the each of the referenced applications are incorporated by reference herein.

GOVERNMENT SUPPORT

The present invention was made with Government support under contract number NIHDR56597, awarded by the National Institute of Health. The Government has certain rights in the invention.

FIELD OF THE INVENTION

The present invention relates in general to compositions and methods for the diagnosis and treatment of autoimmune disorders, especially FcRn-related autoimmune disorders, including but not limited to systemic lupus erythematosus (SLE), insulin resistant diabetes, myasthenia gravis, polyarteritis, cutaneous vasculitis, pemphigus vulgaris, Goodpasture's syndrome, rheumatoid arthritis, Kawasaki's disease and Sjogren's syndrome. In particular, the invention identifies genes and their encoded proteins that are involved in the FcRn pathway for IgG protection. The genes, and their encoded proteins, identified can be used diagnostically, as targets for therapeutic intervention or manipulated for use as model systems for drug discovery in transgenic mice and their related cell lines. The present invention further relates to compositions and methods for FcRn-dependent drug delivery mechanisms. In particular, the invention allows the investigation and characterization of novel transepithelial FcRn-related drug delivery mechanisms using the FcRn manipulated mice and their related cell lines. Additionally, methods and compositions are provided for FcRn-dependent drug stability mechanisms. In particular, the invention allows the investigation and characterization of novel gene-manipulation mechanisms related to the FcRn-pathway for increasing the stability of therapeutics and drugs in vivo.

BACKGROUND OF THE INVENTION

Antibodies have been known since before the 20$^{th}$ century to play an important role in immunological protection against infectious organisms. The immune system cells that produce antibodies are B-lymphocytes. There are four major classes: immunoglobulin M (IgM), IgG, IgA, and IgE, but IgG is by far the most prevalent class, comprising about 90% of all antibodies in adults. Each class of antibody has a specific role in immunity, including primary and secondary immune responses, antigen inactivation and allergic reactions. IgG is the only class of antibody that can pass the placental barrier. Therefore, IgG provides the only antibody protection for newborns until their own immune system is able to contribute to antibody production.

Antibody molecules have two ends. One end is the antigen-specific receptor, which is highly variable and engenders each antibody with the capacity to bind a specific molecular shape. The other end, referred to as Fc, has sequence and structural similarities within a class and confers the ability to bind to receptors on immune cells. In a perfectly operating immune system, the diverse specificities of the antigen specific receptor engenders the host with a diverse repertoire of antibodies with the ability to bind to a wide array of foreign infectious microorganisms, the result being destruction of the microbe and immunity.

Autoimmune diseases occur when the immune system erroneously senses that normal tissue is foreign and attacks it. One of the most prevalent immunological participants in autoimmune destruction is autoantibodies, which are normal antibody molecules that have gone awry and destroy normal tissue. This leads to many types of autoimmune diseases, including systemic lupus erythematosus (SLE). Systemic lupus erythematosus (SLE) is a prototypic disease of systemic antibody dysregulation with the common feature of hypergammaglobulinemia, anti-DNA features and anti-nuclear protein antibodies, and immune complexes that accumulate at many sites including the kidney glomeruli, vascular system, joints and skin (Theofilopolos and Dixon, Adv. Immunol. 37: 296–390 (1985); Theofilopolos and Dixon, Immunol. Rev. 55:179–215 (1981); Boumpas et al, Ann Int. Med. 122:940 (1995)). The severity can range from mild to very severe, from minimally debilitating to lethal.

Treatment of autoimmune diseases usually includes therapy with nonsteroidal anti-inflammatory drugs (NSAID) or corticosteroids, which generally suppress the immune system by, for example, inhibiting mediators of the inflammatory process. Although effective, there are many potentially harmful side effects associated with these treatments, including stomach erosions, bleeding ulcers, high blood pressure and hepatic, and renal dysfunction. In cases where renal function is severely impaired, kidney transplants only provide temporary relief because of the systemic nature of the autoimmune disease. The identification of less radical and more specific methods of prevention and treatment of SLE is thus a matter of considerable importance.

One of the most promising new treatments for autoimmune diseases is the periodic administration of patients with high doses of antibodies. This treatment is very expensive and yields only transient relief, but relative to other treatment regimens available is highly effective with lower incidences of harmful side effects. The administration of high doses of antibodies into a patient with a disease caused by antibodies seems contradictory. However, the identification of the mechanism by which high dose antibody treatments work, and targeting that mechanism directly, could lead to far more effective therapies to treat autoimmune disease.

One such hypothesis involves the endothelial receptor FcRn (FcRp/Fcgrt1). FcRn is a novel member of a family of proteins that perform varied immunological functions. It is known that the FcRn molecule is expressed in the vascular endothelium along with other tissues of adult animals, including mice and humans. FcRn binds to antibody molecules, but only those from the IgG class. Bjorkman and Simister (PNAS 89:638–42, 1992) solved the crystal structure of the FcRn/IgG complex, proving that a receptor/ligand relationship exists between the two molecules.

Most molecules, including antibodies, only remain a short amount of time in the circulation because they are captured by vascular endothelial cells and then efficiently destroyed by a process referred to as catabolism. The existence of a receptor for IgG molecules which greatly slows catabolism of the IgG molecules has been previously proposed. The proposed receptor is postulated to do this by binding most IgG molecules before they are destroyed, and then recycling the antibodies back into the bloodstream thereby increasing the half-life of IgG. Several investigators have indirectly demonstrated such a protective effect by coupling the Fc region of IgG to different polypeptides to improve stability of the polypeptide (U.S. Pat. No. 6,096,871, U.S. Pat. No. 6,121,022). In addition, PCT Application WO 97/34631 describes the use of immunoglobulin-like domains in increasing the stability and longevity of pharmaceutical compositions for therapeutic and diagnostic purposes.

SUMMARY OF THE INVENTION

One aspect of the present invention relates to a transgenic knockout mouse whose genome comprises a homozygous disruption in its endogenous FcRn gene, referred to herein as muFcRn-/-. The homozygous disruption of the FcRn gene prevents the expression of a functional muFcRn protein. This results in the mouse having substantially increased catabolism of IgG molecules, and therefore shorter lived IgG antibodies.

Another aspect of the present invention relates to cells derived from the muFcRn-/-, described above. These cells contain the same homozygous disruption in their FcRn gene as the whole animal from which they are derived. Particularly useful cells include, without limitation, endothelial cells, epithelial cells, fibroblasts, leukocytes, and liver hepatocytes. Such cells are useful in assay systems for identifying therapeutic agents described herein.

The present invention also relates to a method for generating a monoclonal antibody to the FcRn protein, especially human and mouse FcRn, but including other mammals such as dogs, cats, horses, cows and sheep. The method is performed by immunizing the mouse with an FcRn protein (preferably human or mouse FcRn, but also including other mammalian FcRn such as from dogs, cats, horses, cows and sheep), or an antigenic fragment thereof, and generating a hybridoma which secretes a monoclonal antibody which specifically binds the FcRn protein, from B-cells of the immunized mouse by otherwise standard means known to those of skill in the art.

Another aspect of the present invention relates to the monoclonal antibody which specifically binds FcRn, the monoclonal antibody being generated in the FcRn-/- mouse. The monoclonal antibody generated in the FcRn-/- mouse will bind FcRn with at least 10-fold higher avidity than monoclonal antibodies presently available (Raghavan et al. Immunity 1: 303–315 (1994)).

Additional aspects of the present invention are discussed more fully in the Detailed Description Section which follows.

DETAILED DESCRIPTION OF THE INVENTION

Figure 1:
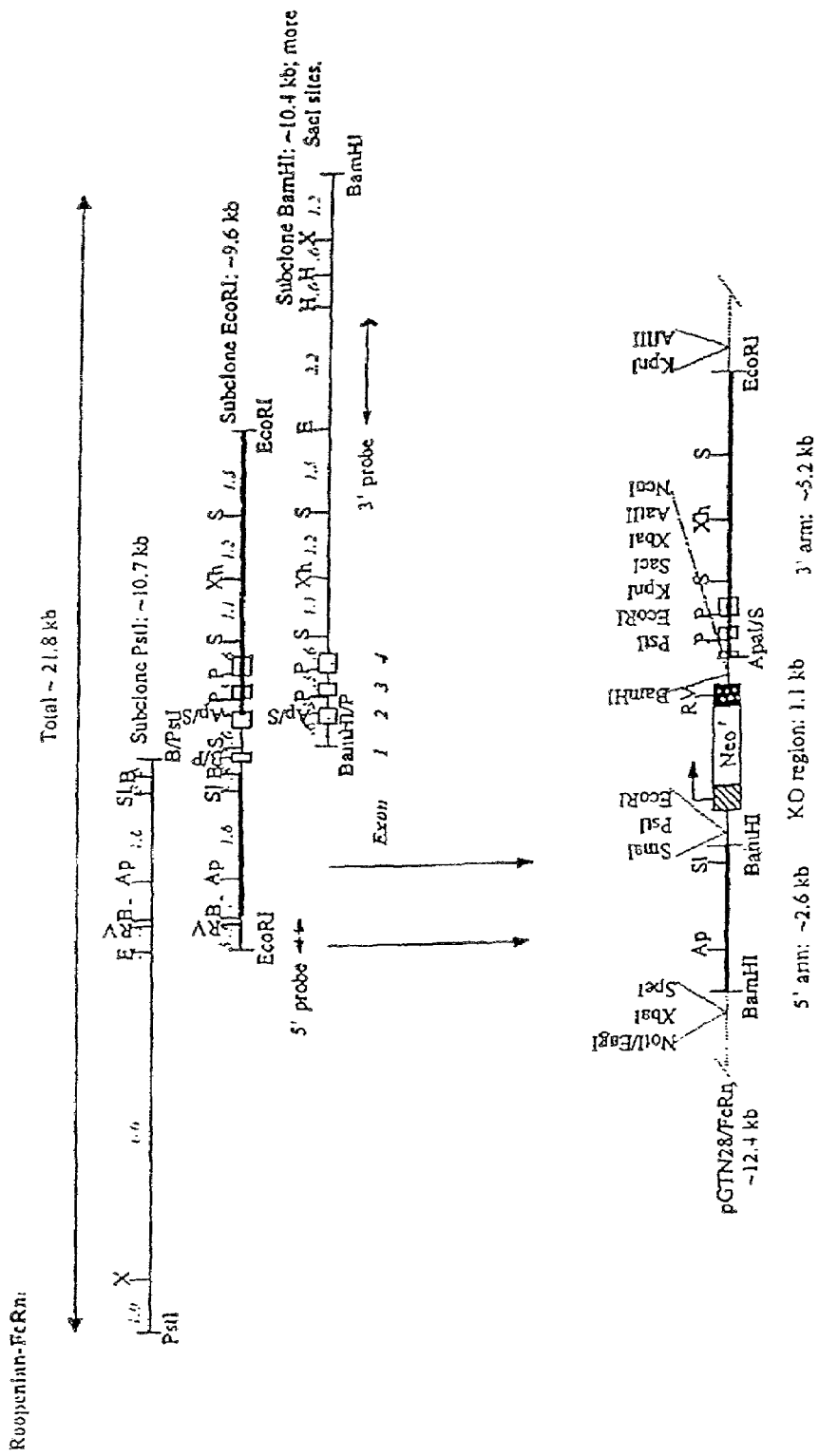
FIG. 1 is a diagram of the targeting vector used to produce targeted disruption of the FcRn gene.
Figure 2:
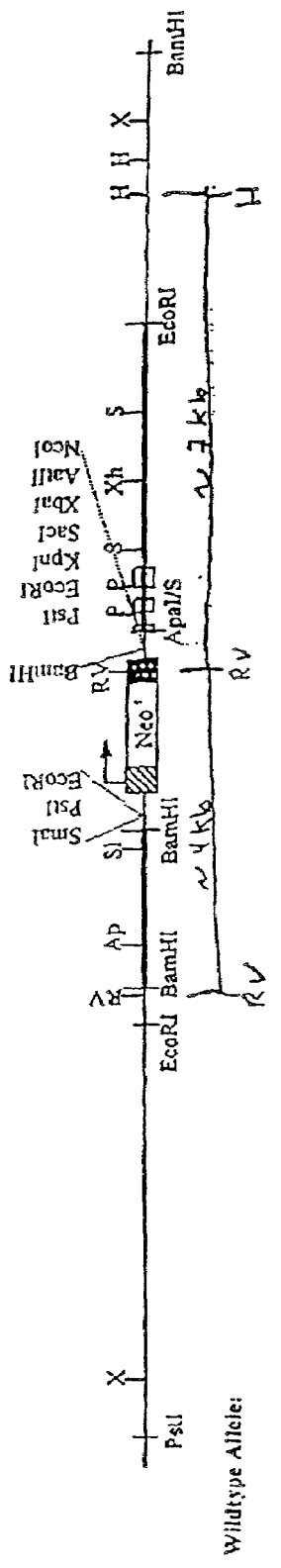
FIG. 2 is a diagram of the strategy used to identify the FcRn recombinant allele produced by proper targeted disruption of the FcRn gene by the targeting vector.
Figure 2:
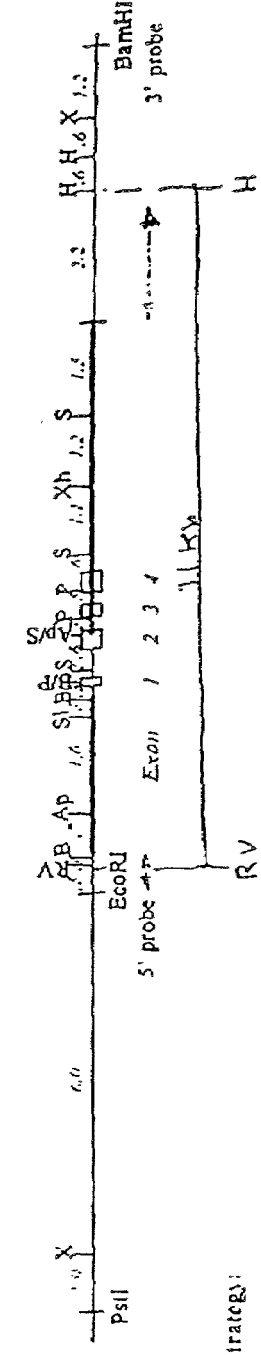

Aspects of the present invention are based on the conclusive finding that FcRn functions as a Fc-dependent IgG protection receptor which selectively protects antibodies of the IgG isotype from normal protein catabolism. This finding indicates that inhibition of Fc protection is an effective treatment for diseases which are precipitated by hypergammaglobulinemia.

One aspect of the present invention relates to a transgenic knockout mouse whose genome comprises a homozygous disruption in its endogenous FcRn gene, referred to herein as muFcRn-/-. The homozygous disruption of the FcRn gene prevents the expression of a functional muFcRn protein. This results in the mouse having substantially increased catabolism of IgG molecules, and therefore shorter lived IgG antibodies. IgG isotypes, such as mouse IgG1, IgG2a, IgG2b, and IgG3 molecules in addition to human IgG1, IgG2 and IgG4, are expected to be protected by FcRn. This phenotype may be conclusively identified through quantitation of exogenously added IgG, preferably IgG1, to determine the half-life in the mouse. The IgG antibody administered to the FcRn-/- mouse exhibits a substantially shorter half-life than the same antibody administered to an appropriate control mouse. An appropriate control mouse is a littermate that has at least one copy of the endogenous FcRn gene. Such a control mouse is also referred to herein as a wild-type mouse. Unless otherwise indicated, a substantial difference as referred to herein (e.g. a substantially shorter half-life), is a detectable, reproducible, statistically significant difference as compared to the same determination in an appropriate control. In the Exemplification section below, a greater than 5-fold shortening of the determined half-life of exogenous IgG1 was observed in the muFcRn−/− mouse, as compared to a control mouse. In addition to the increased catabolism of IgG molecules, the muFcRn−/− mouse was unable to absorb maternal IgG in the neonatal stage of development.

In one embodiment, homozygous disruption of the FcRn gene results from deletion of a portion of the endogenous FcRn gene. The portion deleted is any portion of the coding or non-coding sequences necessary for expression of a functional FcRn molecule. Preferably, the deletion results in the absence of any synthesized FcRn protein product. However, synthesis of a non-functional FcRn is also expected to produce a mouse with the same phenotype.

The deleted portion is preferably replaced with a nucleic acid sequence which contains an identifiable marker, such as resistance to a toxic molecule (e.g., a neomycin-resistance cassette). The muFcRn−/− mouse described in the Exemplification section below has a homozygous disruption which consists of a deletion of 853 nucleotides upstream of exon 1, the entirety of exon 1 and intron 1, and 207 nucleotides immediately downstream of intron 2 of the FcRn gene. The deleted portion of the gene is replaced with a neomycin-resistance cassette. Those of skill in the art will recognize that functional disruption of the FcRn gene may also be accomplished with other approaches (e.g., introducing sequences into the gene which disrupt transcription or translation).

Another aspect of the present invention, is cells derived from the muFcRn−/−, described above. These cells contain the same homozygous disruption in their FcRn gene as the whole animal from which they are derived. Particularly useful cells include, without limitation, endothelial cells, epithelial cells, fibroblasts, leukocytes, and liver hepatocytes. Such cells are useful in assay systems for identifying therapeutic agents described herein.

The muFcRn−/− mouse has several utilities. One such utility is in the production of a monoclonal antibody which specifically binds FcRn with high avidity, preferably human FcRn. Prior to the present invention, antibodies (both polyclonal and monoclonal) which bind with high avidity to mouse FcRn and human FcRn were not available. This was due to the difficulties involved in generating a strong humoral response to such a highly conserved protein. This obstacle is overcome by generating the antibodies in the FcRn−/− mouse, since the mouse will not recognize FcRn as a self antigen.

Therefore, another aspect of the present invention relates to a method for generating a monoclonal antibody to the FcRn protein, especially human and mouse FcRn, but including other mammals such as dogs, cats, horses, cows and sheep. The method is performed by immunizing the mouse with an FcRn protein (preferably human or mouse FcRn, but also including other mammalian FcRn such as from dogs, cats, horses, cows and sheep), or an antigenic fragment thereof, and generating a hybridoma which secretes a monoclonal antibody which specifically binds the FcRn protein, from B-cells of the immunized mouse by otherwise standard means known to those of skill in the art.

The description of FcRn as binding to antibody, as used herein, refers to the inherent binding of FcRn to the Fc region of antibodies of the IgG isotype whereby FcRn protects IgG antibodies from degradation. Antibodies, regardless of their antigen binding regions, can be bound by FcRn, provided that they are of the IgG isotype and in an acidic (~pH6) environment. This function of FcRn is exploited therapeutically in IVIg treatment. Conversely, the description of the monoclonal antibody from the present invention, which binds to FcRn, refers to binding of the monoclonal antibody via its antigen receptor specifically to antigenic sites on the FcRn molecule independent of the environmental pH. This type of binding is distinct from the above mechanism described for IVIg treatment since the antigen receptor end of the antibody is employed for binding to FcRn, rather than its Fc region as seen in FcRn binding to IgG isotypes. Such clonally unique antibodies are typically generated in a humoral immune response to the FcRn molecule, or an antigenic fragment thereof.

Another aspect of the present invention relates to the monoclonal antibody which specifically binds FcRn, the monoclonal antibody being generated in the FcRn−/− mouse. The monoclonal antibody generated in the FcRn−/− mouse will bind FcRn with at least 10-fold higher avidity than monoclonal antibodies presently available (Raghavan et al. Immunity 1: 303–315 (1994)). Preferably, the monoclonal antibody binds FcRn at a position which is critical for binding IgG-Fc, so that when the antibody is bound, FcRn binding of IgG-Fc is inhibited. Inhibiting binding of FcRn to the IgG Fc region will decrease FcRn mediated IgG protection from catabolism. This decrease in protection is therapeutically useful in treatment of autoimmune diseases, as discussed below.

Preferably, the antibody of the present invention binds the FcRn-β2M complex, since it is in the context of this complex that FcRn binds IgG-Fc. Since the FcRn-β2M complex is the context which allows FcRn to bind the Fc region of IgG, blocking the formation of the FcRn-β2M complex is another means to decrease FcRn mediated IgG protection. Therefore, another aspect of the invention relates to monoclonal antibodies which inhibit binding of β2M to FcRn. Preferably, the monoclonal antibody binds FcRn at a position which is critical for β2M binding.

Monoclonal antibodies which strongly bind the FcRn protein are useful diagnostic tools. Detection of FcRn in a patient or individual may be important in determining the extent of participation that FcRn plays in any autoimmune disease process, as well as the presence of FcRn in all model systems described herein. Detection using the monoclonal antibodies to FcRn described above can be accomplished using a variety of methods. Those of skill in the art will recognize that many immunological methods exist to detect polypeptides with an antibody-based system. These include, but are not limited to, enzyme-linked immunosorbent assay (ELISA), radioimmunoassay (RIA), antibody-based lateral flow assays, and flow-cytometry assays. The preferred embodiment comprises a solid support, such as a microtiter well, filter, membrane, column or beads, where sample is bound either covalently or non-covalently to the solid support. The sample could consist of blood, tissue, cells or other biological sample used in the model systems, or found in an individual or patient. Anti-FcRn monoclonal antibody is then added, and if FcRn is present in the sample, will bind to the protein bound to the solid support. If the MAb-FcRn complex is present, then an antibody that recognizes the monoclonal antibody, e.g. goat-Anti mouse Ab, will also bind onto the solid support. This secondary antibody will be preferably linked to a tracer agent, such as a fluorophore or chemical agent. Other tracers include gold, radioactive elements and enzymes that react to give a detectable signal indicating the presence of FcRn.

Since the monoclonal antibody of the present invention binds FcRn with high specificity and avidity, the antibody itself would be highly useful as a therapeutic, to inhibit the protecting effects of FcRn on IgG catabolism. Therefore, another aspect of this invention is the use of the monoclonal antibody as an inhibitor of FcRn-mediated IgG protection. The antibody would be administered to the patient in sufficient doses to inhibit FcRn-mediated IgG protection, which consequently relieves symptoms associated with hypergammaglobulinemia conditions. These conditions include, but are not limited to, systemic lupus erythematosus, insulin resistant diabetes, myasthenia gravis, polyarteritis, cutaneous vasculitis, pemphigus vulgaris, Goodpasture's syndrome, rheumatoid arthritis, Kawasaki's disease, and Sjogren's syndrome. The dosage used will be established in a fashion consistent with good medical practice, taking into account the individual patient, the site of delivery, the method of administration and other factors well known to medical practitioners.

While mouse antibodies can be injected into hosts of other species, it is preferable that the monoclonal antibodies produced in the muFcRn-/- mouse were engineered to decrease the immunogenicity of the therapeutic in the host that it is used in. Therefore, a further embodiment of the invention comprises the engineering of the monoclonal antibodies to decrease the immunogenicity of the antibodies in the individual patient. There are many techniques well known in the art to accomplish this, including designing chimeric antibodies and CDR-grafting. The term "chimeric" antibody is used herein to describe a polypeptide comprising at least the antigen binding portion of an antibody molecule linked to at least part of another protein (typically an immunoglobulin constant domain). U.S. Pat. Nos. 4,816,567, 5,225,539, 5,530,101, 5,585,089, and 5,693,761 disclose methodologies for humanizing therapeutic monoclonal antibodies by grafting critical portions of the CDR and framework regions of the variable domain, from the monoclonal antibody onto a human immunoglobulin. Therapeutic antibodies used in species other than human will be engineered to be predominantly like the species that it will be injected into.

Given the information provided in the present disclosure, it is possible to produce a monoclonal antibody, produced by methods other than in the FcRn-/- mouse, which specifically binds FcRn and/or the FcRn/β2M complex, to inhibit binding of FcRn to the Fc region of IgG. Such an antibody is also intended to be included in the present invention.

It is also useful to further manipulate the FcRn-/- transgenic knockout mouse to include additional traits useful in the context of the null mutation. One such useful trait is for the mouse to express huFcRn which functions in the mouse to protect IgG from degradation. Such a mouse is herein referred to as muFcRn-/-, +huFcRn. The term "functional FcRn" as used in reference to any FcRn transgenic mouse described herein, is used to describe FcRn which binds the IgG-Fc and protects IgG from degradation. Preferably, huFcRn is expressed at a level similar to endogenous expression. It may also be useful in some circumstances to express FcRn at levels substantially higher than endogenous. Strong expression vectors known in the art are commonly used to produce expression levels of 10- to 100-fold higher than endogenous expression levels.

The expression of functional huFcRn is accomplished for example by generating a FcRn-/- transgenic knockout mouse, which is also transgenic for expression of a complete huFcRn gene. A complete huFcRn gene contains introns, exons, and 5' and 3' sequences necessary and sufficient for expression of the gene in the transgenic mouse. In a preferred embodiment, the huFcRn gene, which is introduced into the mouse as a transgenic, contains all known upstream and downstream non-coding sequences known to play a regulatory role in FcRn gene expression. In a preferred embodiment, the huFcRn gene comprises about 10 kb of sequences from the human genome which flank the huFcRn gene at the 5' end, and about 10 kb of sequences which flank the huFcRn gene at the 3' end. The term "about" as used herein in reference to the size of nucleic acids refers to an amount within ±3 kb.

Alternatively, expression of functional huFcRn is accomplished by expression of FcRn protein from a huFcRn cDNA. The cDNA construct contains regulatory sequences which promote expression in the mouse. Examples of useful promoters are a retrovirus promoter, an adenovirus promoter, an SV40 promoter, and the β-actin promoter. A useful enhancer is the CMV enhancer. In addition, the β-globin intron also has useful regulatory sequences for expression of huFcRn.

The muFcRn-/-, +huFcRn mouse serves as a useful animal model for FcRn-related autoimmune disease in humans. FcRn-related autoimmune diseases have an IgG1 autoantibody involvement. FcRn-related autoimmune diseases can be identified by improvement of a patient/animal model from FcRn targeted therapy. For instance, in animal models, an FcRn-/- mouse generated in an FcRn-related autoimmune disease background should exhibit an improved condition with respect to the disease symptoms and/or pathology. Additionally, FcRn-related autoimmune diseases in humans show clinical improvement with IVIg therapy (e.g., systemic lupus erythematosus, insulin resistant diabetes, myasthenia gravis, polyarteritis, cutaneous vasculitis, pemphigus vulgaris, Goodpasture's syndrome, rheumatoid arthritis, Kawasaki's disease, and Sjogren's syndrome).

The muFcRn-/-, +huFcRn mouse is a useful model system in which to identify therapeutic agents which specifically inhibit huFcRn mediated protection of IgG antibodies in the treatment of FcRn-related autoimmune disease. In addition, the mouse model system can be enhanced for specific diseases by crossing the transgenes onto mouse strains carrying normal or mutant alleles involved in the disease pathway. Those of skill in the art will recognize that expression of genes in mice can be accomplished by a variety of standardized methods (L. Morel, Y. Yu, K. R. Blenman, E. K. Wakeland, Mammal. Genome 7, 335–339 (1996). For example, model systems which are more specific for a particular autoimmune disease can further be generated from the muFcRn-/-, +huFcRn transgenic knockout mouse by producing the knockout mouse on a disease mutant background. A number of mouse strains and mutants are known which exhibit an autoimmune disease phenotype. The mouse mutants NZM2410/J (Morel et al., Immunity 1: 219–229 (1994)), BXSB/MpJ, BXSB/MpJ-Yaa (Murphy et al., Arthritis Rheum. 22: 1188–1194 (1979)), MRL-MPJ, MRL-MPJ-Faslpr (Andrews et al., J. Exp. Med. 148: 1198–1215 (1978); Theofilopolos et al., Adv. Immunol. 37: 296–390 (1985)), all exhibit a SLE disease phenotype. A muFcRn-/-, +huFcRn transgenic knockout generated in either a NZM2410/J, BXSB/MpJ, BXSB/MpJ-Yaa, MRL-MPJ, or MRL-MPJ-Faslpr background will serve as an effective animal model for SLE in humans. As such, the mouse will be useful for identifying, refining and optimizing therapeutics for treatment of SLE in humans. Cells derived from the transgenic knockout mouse made in a disease phenotype mouse background are also useful for in vitro assays for identifying therapeutic agents.

The muFcRn-/-, +huFcRn mouse model can be further enhanced by the introduction of human genes associated with SLE autoimmunity. For example, the human IgG locus can be introduced by "knock in" technology, resulting in muFcRn−/−, +huFcRn mice that produces only human IgG. Additionally, a rearranged human IgG transgenic encoding autoimmune-associated IgG autoantibodies (e.g., antinuclear antibodies) can be introduced transgenically. Those of skill in the art will recognize that introduction of genes by either transgenic or knock-in technology can be accomplished by standardized methods (Braun U, Rajewsky K, Pelanda R, Proc Natl Acad Sci USA 2000 Jun. 20; 97(13): 7429–34).

Another aspect of the invention relates to methods to identify an inhibitor of FcRn mediated protection of IgG antibodies. One such method is an in vitro assay to identify an agent, which binds the FcRn/β2M complex to inhibit IgG-Fc binding by FcRn. This method utilizes an isolated complex of FcRn and β2M retaining the in vivo function of binding IgG-Fc at about pH 6, with release of the bound IgG-Fc occurring upon shift in the pH to about pH 7.2. The term 'about', as used herein with reference to pH, refers to ±0.2 pH value. The FcRn/β2M complex is bound to a solid support such as a microtiter well, filter, membrane, column, or beads. Commonly used materials for solid support are nylon, polystyrene, polypropylene, and agarose. To identify an inhibitor, a candidate inhibitor is first contacted to the complex. Such contacting of molecular components is generally achieved by adding the components together in aqueous solution. Human IgG, known to be bound by FcRn (e.g., IgG1, is then contacted to the complex under conditions appropriate for binding of the complex to the IgG-Fc region of IgG1. Favorable binding conditions can be verified by binding of FcRn to IgG-Fc in the absence of the candidate inhibitor. Inhibition of binding due to the candidate inhibitor is then assayed. This can be identified by comparing binding of the complex to IgG1 in the presence and absence of the candidate inhibitor. A substantial reduction in binding of the complex to the IgG1 in the presence of candidate inhibitor, as compared to binding in the absence of candidate inhibitor, indicates that the candidate inhibitor functions to inhibit FcRn. Quantitative binding determination of the FcRn/β2M complex to the antibody is useful in detecting a statistically significant reduction in binding. Alternatively, a qualitative determination may also be used. Preferably, human FcRn and β2M are used in the identification of the inhibitor.

The isolated complex of FcRn and β2M, which retains the in vivo function of IgG-Fc binding, is preferably produced by in vitro synthesis from engineered nucleic acids encoding the respective proteins. The proteins may be synthesized separately, and then added together to produce the complex. The Exemplification section below outlines methods for producing the FcRn/β2M complex in vitro. Those of skill in the art recognize that additional methods exist which may be used to produce a complex suitable for the in vitro method described directly above. Alternatively, endogenous complex components can be isolated from an appropriate cellular source.

A candidate inhibitor of FcRn, as referred to herein, is an agent, pharmaceutical, drug, or other molecule (e.g., a small organic molecule, protein or nucleic acid), which is suspected of having an activity that interferes with the protection of IgG antibody by FcRn. An inhibitor may be identified by random screening of libraries of candidate inhibitors or by rational design based on the intended mechanism of inhibition. One mechanism of inhibition is to directly inhibit binding of FcRn to IgG-Fc. This may occur via an inhibitor (e.g., an antibody or small organic molecule), binding to and blocking a site on FcRn which is critical for binding of IgG-Fc. Alternatively, inhibition may occur via an inhibitor binding to FcRn to disable the protective function (e.g., prevent or disrupt the FcRn/β2M complex, prevent internalization of the receptor). Rational design of an inhibitor, which functions by binding to FcRn, is discussed in more detail below. Another form of inhibition of FcRn function is inhibition of FcRn expression at any stage of gene expression (e.g., transcription, translation, post-translational processing, protein transport to the membrane). A commonly used inhibitor of transcription or translation is an oligonucleotide or reverse gene construct which has homology to the target gene or mRNA, or other mechanisms of inhibition, including specific targeting of regulator proteins. Those of skill in the art recognize that additional methods exist which may be used to inhibit FcRn expression.

Another assay to identify agents that inhibit FcRn from protecting IgG in vivo is a cell culture assay. Mammalian cells in culture which functionally express FcRn, are either generated or identified from preexisting mammalian cells. Cells suitable for use in this assay are capable of catabolizing IgG, with expression of FcRn in these cells causing a decrease in this catabolism. Functional expression of FcRn as referred to in the context of an in vivo assay, indicates that the FcRn complexes with β2M, and in that complex binds to IgG-Fc and protects the bound IgG from degradation. Preferably, the FcRn is human. To identify the inhibitor, both human IgG and candidate inhibitor are contacted to the cells. The cells are incubated under conditions appropriate and conducive to normal cell function, and are then assayed for IgG catabolism. An appropriate control is the identical cells, identically treated, except for contact to candidate inhibitor. A substantial increase in IgG catabolism in the cells contacted with inhibitor, as compared to IgG catabolism in control cells, is an indication that the candidate inhibitor inhibits FcRn function. Another control for FcRn specificity is the use of cells that do not express FcRn in the presence of candidate inhibitor. No change should be detected in IgG catabolism as compared to IgG catabolism in the absence of candidate inhibitor contacted to FcRn-expressing cells. This assay detects inhibition of FcRn function via binding to IgG, internalization and protection. Additionally, it can also detect inhibition of FcRn expression, either at the transcriptional, translational, or post-translational level.

Cell lines known in the art, and also primary cells, may be used for the cell culture assay. Cells of the muFcRn−/− and also the muFcRn−/−, +huFcRn transgenic knockout mouse may also be useful in such an assay.

Another method for identifying an inhibitor of IgG protection by FcRn is by using the muFcRn−/−, +huFcRn transgenic knockout mouse, described above. Tracer human IgG and tracer human IgA is administered to the mouse. Tracer antibody is specifically labeled (e.g., with radioisotope) or has a specific activity (e.g., specifically binding to TNP (trinitrophenol)), so as to enable the quantitative determination of the amount of exogenously added antibody present in the mouse bloodstream. Prior to, or upon administration of the tracer antibodies, a candidate inhibitor is administered to the mouse. The amount of tracer IgG and tracer IgA is then monitored over time to quantitate the half-life of the tracer antibodies within the mouse. Administration to, and monitoring of tracer IgG and tracer IgA is also performed with an identically treated control muFcRn−/−, +huFcRn transgenic knockout mouse, in the absence of candidate inhibitor. An increase in the half-life of the tracer IgG, but not the tracer IgA, in the mouse which receives candidate inhibitor indicates that the candidate inhibitor functions to inhibit FcRn protection of IgG. The mouse which does not receive candidate inhibitor should not exhibit an increase in the half-life of either the IgG or IgA tracer antibody.

Optimally, the tracer IgG and IgA is administered intravenously. Candidate inhibitor is administered to the mouse by any method which will result in the candidate inhibitor reaching the bloodstream. An efficient route of administration is intravenous injection. The use of alternate routes of administration in the method incorporates an implicit test of candidate inhibitor targeting to the bloodstream as well as activity.

Additional aspects of the present invention relate to inhibiting FcRn function with an agent which inhibits IgG binding by FcRn via mimicking the structure of IgG-Fc. For instance, an excess of isolated Fc region polypeptide, or a fragment thereof which can be bound by FcRn functions to competitively inhibit binding of FcRn to intact IgG antibodies. The Fc region, or fragment thereof may exist as an isolated molecule or alternatively in the context of a larger molecule (e.g., as a fusion protein), as long as it retains the necessary conformation and molecular accessibility to be bound by FcRn. Such a Fc fragment molecule can be produced via genetic engineering and expression in in vitro systems.

Similarly, an excess of exogenously added IgG may be used to saturate FcRn, resulting in increased catabolism of endogenous IgG. Administration of engineered IgG rather than a mixture of antibodies isolated from sera will reduce the risk of transmission of sera born disease, and also provide considerable cost reduction to the patient. Preferably, the IgG is of the same species (e.g. human antibody administered to a human patient) to prevent the generation of a cross species immune response in the patient. This is thought to be the mechanism of successful IVIg therapy. The engineered IgG need not have a complete or functional antigen binding region, but need only be of an isotype which is bound by FcRn (e.g. IgG1).

A monoclonal antibody which specifically binds huFcRn and inhibits binding of huFcRn to IgG, when administered to the individual in sufficient amounts to inhibit binding of huFcRn of the individual to IgG, will also inhibit FcRn mediated IgG protection, as discussed above. Antibodies which bind to FcRn at the site where FcRn binds IgG-Fc, are likely to inhibit FcRn binding, and thus function therapeutically. Antibodies which bind FcRn and prevent the formation of a FcRn-β2M complex are most likely to inhibit binding of IgG-Fc to FcRn. It may be useful to use fragments of such antibodies which retain FcRn binding ability. As described above, it will be necessary to humanize the monoclonal antibodies in order to minimize species cross reactivity in human therapeutic applications.

Small organic molecules can also be designed to specifically interact with FcRn to inhibit Fc binding from the current understanding of the FcRn interaction with IgG-Fc. Preferably, the organic molecule mimics the sites of the FcRn-binding region on IgG-Fc, which should promote binding to the FcRn at the same sites that bind Fc. This type of binding is expected to inhibit binding of FcRn to IgG-Fc, and thus to inhibit FcRn protection of IgG.

To therapeutically inhibit FcRn mediated IgG protection in an individual, one or more of the above discussed inhibitors of FcRn binding are administered to the individual in an amount sufficient to inhibit binding of the FcRn of the individual to IgG of the individual. Administration should result in eventual distribution of the inhibitor to the bloodstream of the individual. Preferably, the inhibitor which is administered is formulated in a pharmaceutically acceptable carrier. Inhibition of FcRn mediated IgG protection is expected to be a therapeutic treatment for a variety of autoimmune diseases with an IgG autoantibody etiology. Examples of Fc-related autoimmune diseases expected to be ameliorated by such treatment include, without limitation, systemic lupus erythematosus, insulin resistant diabetes, myasthenia gravis, polyarteritis, cutaneous vasculitis, pemphigus vulgaris, Goodpasture's syndrome, rheumatoid arthritis, Kawasaki's disease, and Sjogren's syndrome.

Such therapeutic inhibitors of FcRn mediated IgG protection can be identified in the transgenic mouse model systems described herein. The transgenic knockout mouse generated in a particular disease phenotype background are particularly useful for identifying therapeutic agents for the treatment of that disease. For example, the SLE disease susceptible mutant mice, NZM2410/J, BXSB/MpJ, BXSB/MpJ-Yaa, MRL-MPJ, or MRL-MPJ-Faslpr, which are also FcRn−−, +huFcRn, are preferred for identification of therapeutic agents for the treatment of SLE in humans. Mice carrying combinations of other autoimmune disease susceptible normal or mutant mouse, or human genes whose products are known to play a role in the SLE disease pathway, e.g. the genes encoding human IgG, would add additional power to this approach. To identify such a therapeutic agent, a candidate therapeutic agent is administered to the transgenic mouse by a route which ultimately delivers the agent to the bloodstream of the mouse. Upon administration of the agent, the mouse is monitored for SLE development, in comparison to an identical control mouse which has not received the agent. Amelioration of SLE disease development or progression in the mouse which receives the agent, indicates that the agent may be useful for treating SLE. Amelioration of the disease is a significant reduction or reversal of development, or progression of characteristic disease symptoms in the mouse.

Another use of the muFcRn−/−, +huFcRn transgenic knockout is found in the identification and pharmacokinetic characterization of agents for use in FcRn-mediated drug stabilization. Presently, the ability of FcRn to bind to molecules that possess an IgG-Fc region and protect them from degradation, is being explored for possible exploitation in drug delivery. Ultimately, development of a formulation for therapeutic agents which promotes FcRn-mediated protection from catabolism, will enable the formulation of therapeutic agents that have longer half-lives in the bloodstream. This will benefit the patient as it will require lower and less frequent doses of administration. The muFcRn−/−, +huFcRn transgenic knockout mouse is an exceptionally suitable model system for identification and characterization of such an agent.

To identify an agent which promotes FcRn-mediated drug stabilization, suspected or candidate agents are formulated with a trackable composition. The formulation is administered to the muFcRn−/−, +huFcRn transgenic knockout mouse and also to a control mouse (muFcRn−/− transgenic knockout), preferably in a pharmaceutically acceptable carrier. Administration is by any route which delivers the formulation into the bloodstream. The half-life of the formulation in the bloodstream of the recipient mice is then assayed via quantitation of the trackable composition in the bloodstream over time. A substantially longer half-life in the bloodstream of the muFcRn−/−, +huFcRn mouse than the control mouse is an indication that the candidate agent promotes the FcRn-mediated stabilization of the trackable composition, and likely will promote stabilization of a similarly formulated therapeutic agent. A substantially longer half-life is a reproducible, statistically significant increase in half-life, and preferably is at least a 2-fold increase. Preferably, the candidate agent is covalently attached to the trackable composition. The identity of the trackable composition may produce a physiological effect on mouse function, or may simply be an easily detectable molecule (e.g., through enzymatic activity or recognition of or as an antigen).

A likely candidate agent for FcRn-mediated protection is the IgG Fc region, already known to bind FcRn. In addition, smaller regions of Fc which retain the ability to be bound by FcRn may also function to protect an associated therapeutic. Further, molecules which adopt a similar structure to Fc, or have critical sequence homology to Fc may also function to protect an associated therapeutic.

The muFcRn−/−, +huFcRn transgenic knockout may also be used to determine the pharmacokinetics of a known FcRn-mediated stabilizing agent in association with a pharmaceutical, in comparison to the non-associated pharmaceutical. A formulation comprising the pharmaceutical in association with the FcRn-mediated stabilizing agent (e.g., Fc or an Fc derived moiety) is administered to the muFcRn−/−, +huFcRn transgenic knockout mouse. The identically formulated pharmaceutical lacking the FcRn-mediated stabilizing agent is administered to an identical mouse, and the half-lives of the pharmaceutical is determined in each mouse. The respective half-lives are then compared to determine the difference in pharmacokinetics of the pharmaceutical conferred by the FcRn-mediated stabilizing agent. Administration is by any route which delivers the formulation into the bloodstream.

In addition to in vivo-based assays for identification and pharmacokinetic characterization of agents for use in FcRn-mediated drug stabilization, a cell-based assay can be used for high-throughput screening of candidate formulations. For these assays, cell lines known in the art and also primary cells may be used for the cell culture assay. Cells of the muFcRn−/− and also the muFcRn−/−, +huFcRn transgenic knockout mouse may be useful in such an assay.

Functional expression of FcRn in mammalian cells in a microtiter plate or any other suitable format allows for the simultaneous high-throughput screening of multiple compounds, further aiding the identification of novel compositions that stabilize pharmaceutical compounds. Cells suitable for use in this assay will be grown in microtiter plates, filters, membrane, columns, beads, or any other suitable platform. Commonly used materials for solid support are nylon, polystyrene and polypropylene. Suspected or candidate agents are formulated with a trackable composition and added to the microtiter plate wells. The half-life of the formulation in the culture medium is then assayed. A substantially longer half-life of candidate formulations grown in muFcRn−/−, +huFcRn cells than in cells derived from muFcRn−/−, or any other control line that lacks expression of FcRn, indicates that the candidate agent promotes the FcRn-mediated stabilization of the formulated therapeutic agent. A substantially longer half-life is a reproducible, statistically significant increase in half-life. Preferably, the candidate agent is covalently attached to a trackable composition. The identity of the trackable composition may produce a physiological effect on mouse function, or may simply be an easily detectable molecule.

Endogenous FcRn can also be used to deliver an appropriately formulated agent administered non-intravenously to the bloodstream of an individual. Therefore, another aspect of the present invention relates to use of the muFcRn−/−, +huFcRn transgenic knockout mouse as a model system for identification and characterization of an agent which can specifically target a formulation to the bloodstream via huFcRn binding. A formulation comprising a candidate agent for FcRn-mediated drug delivery is attached or associated with a trackable composition. This formulation is administered to a muFcRn−/−, +huFcRn mouse, and also to a muFcRn−/− mouse. The mice are then assayed for the presence of the administered formulation in their bloodstream. Preferably, the assay is quantitative. A substantially higher amount of the formulation in the bloodstream of the mouse which expresses huFcRn is an indication that the candidate agent facilitates FcRn-mediated drug delivery. Routes of administration are any route which is not directly into the bloodstream, and include, without limitation, oral, intranasal, inhalation, and transdermal administration. A substantially higher amount in the bloodstream would be a reproducible, statistically significant increase, which would be at least a 2–5 fold increase. A five-fold or more increase would be considered a strong indication of FcRn-mediated drug delivery. Such agents are likely to be bound by FcRn in a similar fashion as IgG-Fc. Agents which are identified or suspected of functioning in FcRn-mediated drug stabilization, are also likely to function in FcRn-mediated drug delivery.

The ability of IgG-Fc, or any other structurally- or sequence-similar molecule, to target pharmaceutical compositions to the bloodstream via the FcRn protein is especially relevant to the perinatal treatment of fetuses and neonates. Previous work has shown that FcRn is responsible for the active transport of IgG across the placenta (Story, C. M. et al, J. Exp. Med., 80:2377–2381, 1994). In addition, the FcRn protein in neonate gut actively transports digested IgG into the bloodstream, protecting the neonate against enteric infection. (Simister et al, Nature, 337:184–187, 1989). Therapeutics for perinatal correction of disease states, such as metabolic disorders or enzyme deficiencies, could be greatly simplified by using the FcRn pathway for the delivery of pharmaceutical compositions. In the fetus, ingestion of an IgG-Fc, or any other structurally- or sequence-similar molecule coupled to the therapeutic, could be ingested by the mother, which would be transmitted to the fetus via FcRn receptors in the placenta. In neonates, therapeutics could be administered orally or by any other suitable method, bypassing the need to either use intravenous or intramuscular administration. Potential pharmaceutical compositions for use in fetuses or neonates could be tested for their ability to transmit and target the therapeutic in the muFcRn−/−, +huFcRn and muFcRn−/− neonate or fetus mouse as described above.

EXEMPLIFICATION

Previous Characterization of FcRn

FcRn is a distant member of the MHC class I gene family. Like all other class I paralogues, FcRn is a transmembrane protein, and forms an obligate heterodimer with β2 microglobulin (β2M) in order to be transported to the plasma membrane. FcRn was originally identified by Simister and colleagues (Simister and Mostov, Nature 337: 184–7 (1989); Simister and Ahouse, Res. Immunol. 147: 333–7; discussion 353 (1996)). Their findings suggested that FcRn is the neonatal Fc receptor earlier suggested to be involved in the transport of maternal IgG from the gut lumen into the rodent neonatal bloodstream (Simister and Mostov, Nature 337: 184–7 (1989); Simister and Ahouse, Res. Immunol. 147: 333–7; discussion 353 (1996)). FcRn is expressed in the human placental trophoblast, and evidence suggests that it may be the molecule responsible for transplacental transport of IgG in humans (Simister et al., Eur. J. Immunol. 26: 1527–31 (1996); Leach et al., J. Immunol. 157: 3317–3322 (1996)). Both mRNA expression analysis and Western blot analysis indicate that the FcRn gene is widely expressed throughout the body, with highest expression levels being in the liver, proximal small intestine, kidney lung, and placenta. Western blot analysis using rabbit anti-rodent and rabbit anti-human heteroantisera is in general agreement (Simister et al., Eur. J. Immunol. 26: 1527–31 (1996); Simister and Story, J. Reprod. Immunol. 37: 1–23 (1997); Ghetie et al., Eur. J. Immunol. 26: 690–696 (1996); Leach et al., J. Immunol. 157: 3317–22 (1996)).

Biochemical and crystallographic analysis indicate that FcRn binds the Fc region of IgG (Burmeister et al., Nature (Lond.) 372: 336–343 (1994); Ghetie and Ward, Annu. Rev. Immunol. 18: 739–66 (2000); Burmeister et al., Nature 372: 336–43 (1994)). Binding only occurs in an acidic (pH 5–6) environment, such as that found in the intestinal lumen of the neonatal rodent. Rat and human crystal structures indicate that the putative peptide cleft of FcRn is closed, thus preventing peptides from binding (Burmeister et al., Nature (Lond.) 372: 336–343 (1994); West and Bjorkman, Biochemistry 39: 9698–708 (2000)). Both co-crystal structures of rat FcRn/IgG and site specific mutagenesis have mapped the critical sites of interaction of the rodent FcRn with those of the Fc region of IgG (Kim et al., Eur. J. Immunol. 29: 2819–25 (1999); Ghetie et al., Nat. Biotechnol. 15: 637–40 (1997)). The human FcRn (huFcRn) crystal resolved in the absence of IgG is consistent with the same overall binding site, but amino acid differences may affect IgG subclass specificity.

Neonatal Transgenic Mice Deficient in FcRn are Unable to Absorb Maternal IgG

Figure 3:
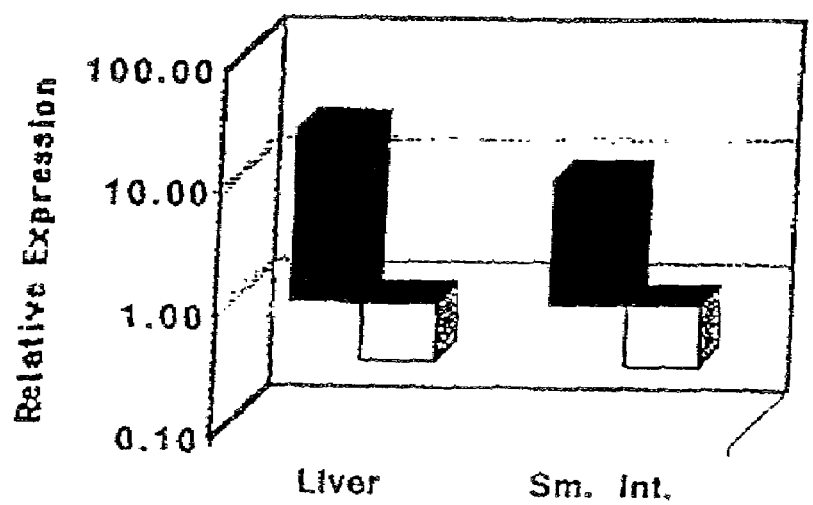
FIG. 3 is a graphical representation of FcRn transcription in wild type versus the FcRn knockout mouse determined by PCR analysis. FcRn+/+ mouse, Dark bars; FcRn-/- mouse, light bars.
Figure 4:
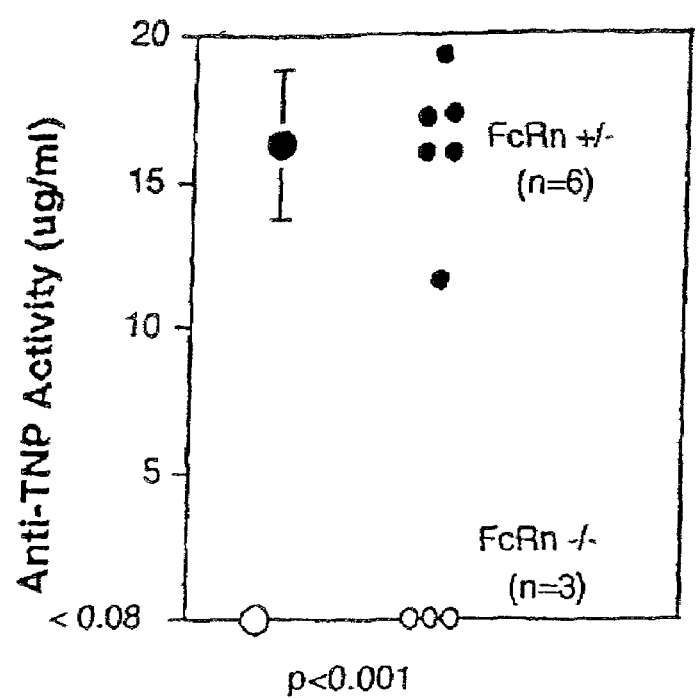
FIG. 4 is a graphical representation of the amount of absorption of maternal IgG to mouse fetal pups. FcRn+/- mice are compared to FcRn-/- mice.

While there is compelling evidence that FcRn binds IgG, the possibility remains that another class I molecule or several class I molecules are responsible for perinatal uptake of maternal IgG. To address this question directly, transgenic mice deficient FcRn were generated by gene targeting methods. The FcRn-deficient mice (FcRn−−) are homozygous for the loss of a genomic fragment that includes FcRn exon 1 and all but the last 3 nucleotides of exon 2. RT-PCR indicates that the FcRn−/− mice fail to transcribe exons 1 and 2, and real-time quantitative RT-PCR analysis indicates that the mice fail to express appreciable levels of FcRn 3' exon 3->4 transcripts (FIG. 3). Importantly, FcRn-deficient (FcRn−/−) neonatal mice are unable to absorb maternal IgG (FIG. 4). These results indicate that FcRn is required for neonatal mice to take up maternal IgG, and conversely, that the mice are completely defective in transplacental and trans-intestinal IgG transport.

FcRn Plays a Role in SLE

In addition to its role as the perinatal IgG transport receptor, an increasing body of evidence suggests that FcRn may be the protection receptor hypothesized by Brambell to protect IgG from catabolism in animals of all ages (reviewed in Ghetie and Ward, Annu. Rev. Immunol. 18: 739–66 (2000); Jungans, R. P., Immunologic Research 16/1: 29–57 (1997)). Over 30 years ago, Brambell noted that IgG was catabolized at a much slower rate than other serum proteins, and proposed the existence of a receptor that preserved IgG (Ghetie and Ward, Annu. Rev. Immunol. 18: 739–66 (2000); Jungans, R. P., Immunologic Research 16/1: 29–57 (1997); Brambell et al., Nature 203: 1352–5 (1964); Brambell, F. W., Lancet. 2: 1087–93 (1966)), calling the hypothesized receptor FcRp. His model proposed that IgG molecules in the bloodstream along with other serum proteins are taken up by normal pinocytosis by tissue, including the vascular endothelium. In the acidic environment of the early endosome IgG binds via its Fc region to FcRp. Then, rather than proceeding through the endosomal catabolic pathway, as is the fate of other serum proteins, the protected IgG molecule is shuttled back to the plasma membrane where it encounters the neutral pH of the extracellular environment, causing release into the blood. Many studies have confirmed and extended this general model, including the proposed existence of an FcRp molecule. Importantly, FcRp exhibited saturation kinetics, in that FcRp lost the ability to protect IgG at high IgG concentrations. However, the molecular identity of FcRp remained unknown.

As discussed above, FcRn forms an obligate heterodimer with $\beta 2M$. $\beta 2M$ has been implicated as involved in SLE disease development by the observation that $\beta 2M$-deficient mice clear IgG at a rate similar to other serum proteins, while $\beta 2M$-intact mice cleared IgG much more slowly (Ghetie et al., Eur. J. Immunol. 26: 690–696 (1996); Junghans and Anderson, Proc. Natl. Acad. Sci. USA 93: 5512–6 (1996)). The $\beta 2M$-deficient mice were also protected from SLE. This resistance was first observed in an experimentally induced form of SLE (Moses et al., Science 261: 91–93 (1993)), followed by genetically determined forms arising on the SLE predisposed MRL-Fas+MRL-Fas$^{lpr}$ and BXSB genetic backgrounds (Christianson et al., J. Immunol. 176: 4933–39 (1996); Christianson et al., J. Immunol. 159: 4781–92 (1997)). If deficient in $\beta 2M$, the mice also failed to develop hypergammaglobulinemia and autoantibodies. The involvement of a molecule known to form a heterodimer with FcRn, suggested that FcRn may also be involved in SLE disease development. Further, since hypergammaglobulinemia is an important component of SLE, and FcRn was known to bind IgG, these studies suggested that FcRn may be an important molecule in the pathogenesis of SLE. Studies using a bullous pemphigoid mouse model supported and extended the hypothesized role of $\beta 2M$ in SLE by showing that $\beta 2M$-deficient mice were protected from developing skin lesions normally observed as a consequence of the systemic administration of pathogenic anti-desmosome IgG Abs (Liu et al., J. Exp. Med. 186: 777–83 (1997)). IgG Fc region mutagenesis experiments (Kim et al., Eur. J. Immunol. 29: 2819–25 (1999); Ghetie et al., Nat. Biotechnol. 15: 637–40 (1997)) suggested that the same residues which interact with FcRn were important for protection of IgG from catabolism. However, because the $\beta 2M$ molecule is known to also bind other class I molecules, the likelihood that a class I molecule other than FcRn is the FcRp remained a distinct possibility. Due to the lack of direct evidence, the role of FcRn in IgG protection and SLE has remained controversial in the art (Singer et al., Eur. J. Immunol. 29: 2259–68 (1999)).

Figure 5:
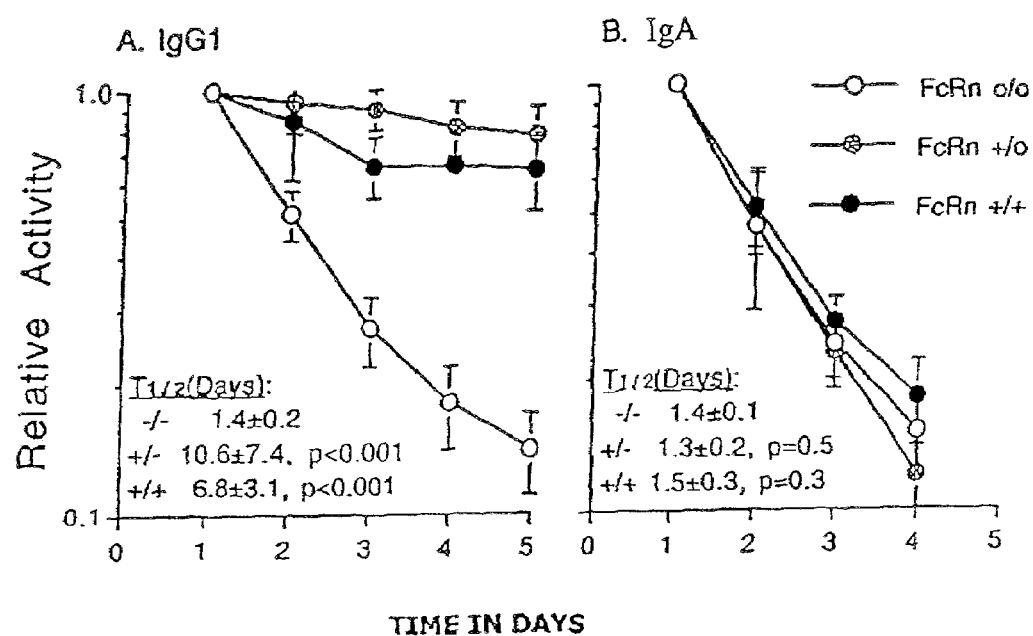
FIG. 5 is a graphical representation of the amount of administered IgG and IgA antibody present in a mouse over 5 days post administration. A. IgG1; B. IgA. Data are represented as the fraction of anti-TNP mAb remaining normalized to the day 1 determination, and are the mean±standard deviation of serum samples from 5 muFcRn-/- and 5 muFcRn+/- mice. In some cases the standard errors are smaller than the plot symbols. Tracer half-lives ($T_{1/2}$) computed are indicated. P values vs. FcRn-/- mice were computed using the one-sided Student's T Test.

To more directly investigate the role of FcRn in IgG protection than had previously been accomplished, the IgG clearance of the FcRn-deficient mice was determined and compared to IgG clearance of mice expressing FcRn. As shown in FIG. 5, IgG clearance was substantially increased in FcRn−/− and $\beta 2M$−/− mice, but IgG was retained in heterozygous (FcRn+/−) littermate controls. In contrast, IgA, which does not bind FcRn, was cleared at the same rate in all mice examined. These results, coupled with the evidence already present in the prior art, conclusively indicate that FcRn is in fact the FcRp molecule.

Endogenous levels of specific Ig isotypes in the mice were also examined. Preliminary results are shown below in Table 1.

TABLE 1

| Genotype | (n) | IgM | IgG1 | IgG2a | IgA |
|---|---|---|---|---|---|
| FcRn −/− | (5) | 234 ± 97 | 9 ± 5 | 34 ± 22 | 48 ± 22 |
| FcRn +/− | (5) | 197 ± 65 | 134 ± 105 | 77 ± 26 | 26 ± 18 |
|  |  | FcRn +/− vs FcRn −/− $p < 0.5$ | FcRn +/− vs FcRn −/− $p < 0.01$ | FcRn +/− vs FcRn −/− $p < 0.01$ | FcRn +/− vs FcRn −/− $p < 0.9$ |
| β2M −/− | (5) | 298 ± 36 | 13 ± 3 | 35 ± 21 | 32 ± 11 |
|  |  | β2M −/− vs FcRn −/− | β2M −/− vs FcRn −/− | β2M −/− vs FcRn −/− | β2M −/− vs FcRn −/− |

Despite the variability among mice (presumably because of the heterogenous genetics of the mouse stocks), the results are consistent with an important role for FcRn in selectively protecting IgG isotype Abs. In spite of their lower IgG concentrations, FcRn−/− mice appeared to have an otherwise normal phenotype. Gross anatomy, lymphoid cellularity, and leukocyte subset numbers (determined by FACS) of 10 week old FcRn−/− founders was indistinguishable from wild-type littermates. These results are consistent with the predicted selectivity of the action of FcRn, and indicate that FcRn-deficiency does not result in unexpected pleiotropic effects. All evidence to date indicates that FcRn is peripheral to central immune system function, in that it has evolved solely to transport and protect IgG. These observations indicate that specific targeting of FcRn function will be a safe and effective therapeutic in the treatment of FcRn related autoimmune diseases such as SLE.

Figure 8:
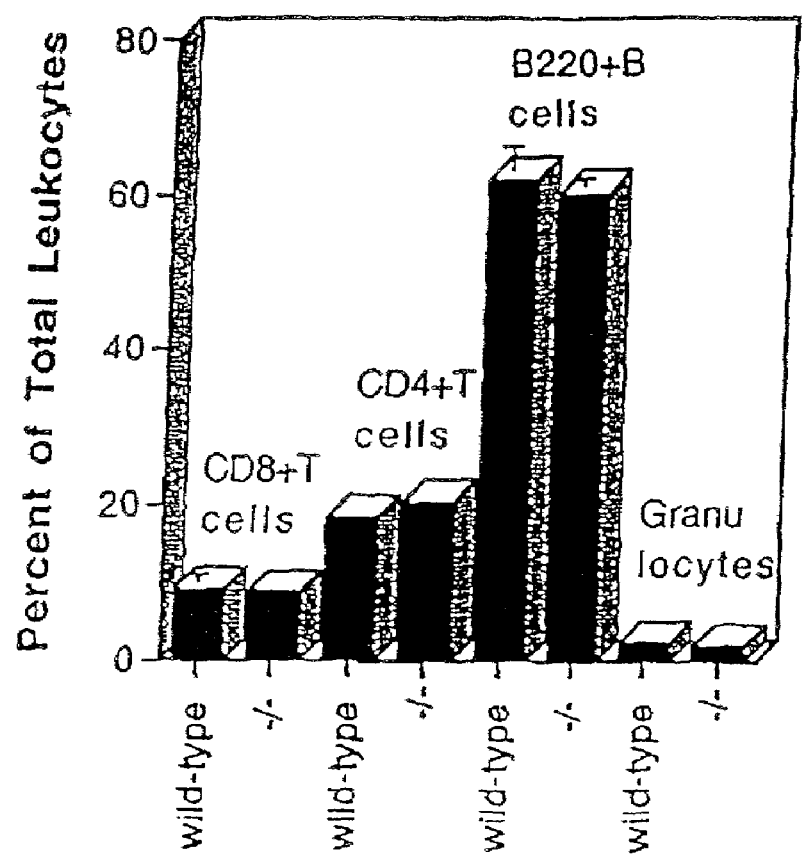
FIG. 8 is a bar graph indicating the relative amounts of leukocyte spleen cell subsets in the indicated mice. muFcRn+/+ and muFcRn+/- mice were used as wild type. Data shown are the mean standard deviation of 3 muFcRn-/- or wild-type mice.

Analysis of spleen cells from the FcRn−/− mice as compared to wild type mice indicates that the FcRn deficiency does not affect the frequency of dominant leukocyte spleen cell subsets present in the mice, as indicated in FIG. 8.

The Clinical Efficacy of IVIG is Due to Saturation of FcRn

Ongoing studies directed toward understanding the progression of SLE disease in mice deficient in FcRn will complement the above results and progress toward developing methods of therapeutic treatment of SLE and other FcRn related autoimmune diseases, by specifically targeting the function of the FcRn molecule. In addition, existing therapies can be directed to more specifically target FcRp, increasing efficiency and decreasing cost of treatment. One such therapy, intravenous immunoglobulin (IVIG) therapy, is a purified human plasma product that is receiving increased usage in the clinic either alone or as an adjunct in the treatment of a wide array of autoimmune diseases, including myasthenia gravis, Kawasaki's disease, idiopathic thrombocytopenic purpora, Guillain-Barre syndrome, multiple sclerosis, rheumatoid arthritis, and SLE. The success of IVIg in a wide range of autoimmune diseases suggests a generic mode of action. IVIg treatment results in clinical improvement of autoimmune diseases which have a considerable autoAb involvement, ranging from organ specific (e.g., mysethenia gravis) to systemic (e.g., SLE). The findings presented herein with respect to FcRn's involvement in SLE and other autoimmune diseases indicate that the mechanism of action of IVIG is to saturate FcRn, in turn, purging the individual of endogenous pathogenic autoAbs by forcing their catabolism. The therapeutic effects currently obtained with IVIg administration can be achieved by administration of IgG antibodies produced artificially, thus reducing costs and dangers associated with administration of products derived from human blood.

Mice Deficient in FcRn are Protected from SLE

"Speed congenic" backcrossing will be used to transfer the FcRn-null mutation onto NZM2410/J, BXSB/MpJ, BXSB/MpJ-Yaa, MRL-MPJ, or MRL-MPJ-Faslpr backgrounds, from which colonies of FcRn−/− mice will be established. This method involves the genotyping of backcross and selection of progeny which lack the greatest number of donor genome alleles (Morel et al., Mammal. Genome. 7: 335–339 (1996)). MRL-MPJ-Faslpr mice develop a very severe SLE-like syndrome accompanied by a lymphoproliferative syndrome as a consequence of the Fas$_{lpr}$ mutation in combination with SLE-predisposed MRL background genes. Previous studies have indicated that several facets of the SLE disease are ameliorated in β2M-deficient MRL-MPJ-Faslpr mice. NZM2410/J mice develop a less acute form of SLE, with many features in common with human SLE (Morel et al., Mammal. Genome. 7: 335–339 (1996); Morel et al., Immunity 1: 219–29 (1994)). A deficiency of FcRn is expected to protect mice of these backgrounds from disease development. Procedures conducted previously analyzing SLE in the β2M-deficient mice (Christianson et al., J. Immunol. 176: 4933–39 (1996); Christianson et al., J. Immunol. 159: 4781–92 (1997)), will be followed to confirm this expectation. Groups of sex-matched FcRn−/− and wild-type mice will be monitored for general condition (weight, vigor, coat, skin lesions) twice a week, and serum will be taken on a semi-weekly to monthly basis. FcRn−/− mice in a SLE disease background and control FcRn+/− mice made in a SLE disease background, will be sacrificed at 5 months of age, and the remainder will be monitored for lifespan studies. Similar analyses will be carried out for the various SLE disease strains, but owing to more chronic disease progression, the less severe strains for histopathological analysis will be sacrificed at 8 months. Levels of serum Ig, IgM, IgG1, IgG2a, and IgG2b will be monitored by ELISA. SLE-related serum parameters, such as proteinuria, serum creatinine, and blood nitrogen urea will be analyzed using a blood chemistry analyzer. Antinuclear antibodies will be measured using clinical human antinuclear antibody ELISA kits from Hemagen Inc. adapted for mouse use (Christianson et al., J. Immunol. 176: 4933–39 (1996)). Tissues (lymph node, spleen, kidney, liver, and lung) will be fixed and stained with H&E and Periodic Acid Schiff (PAS). To monitor glomerular immune complex deposition and lymph node B cell follicles, cryostat sections will be prepared and stained directly with FITC goat-anti-mouse IgM, IgG, and C3 (kidney only). Histological interpretations will be carried out by The Jackson Laboratory Pathology Service.

Because FcRn is an important molecule for protection from SLE, the FcRn-deficient mice with a SLE disease background are expected to be considerably more resistant to SLE than controls. By comparing the disease properties of these mice with published studies on β2M-deficient mice, specific aspects of SLE disease progression that are directly caused by FcRn function will be determined, and otherwise disassociated from potential effects caused by other β2M-dependent molecules.

Development of Mouse Models for SLE

Figure 6:
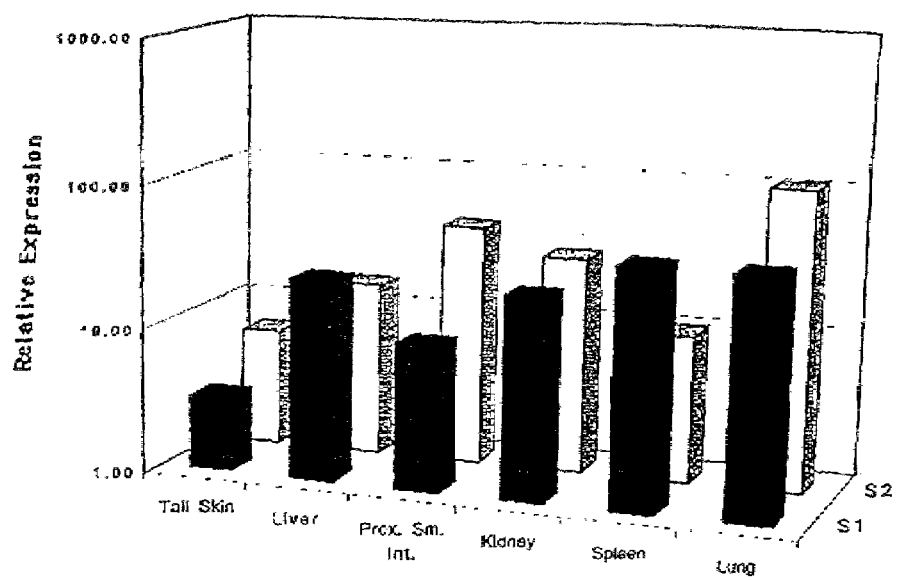
FIG. 6 is a bar graph which quantitatively represents the expression of FcRn RNA in the tissues of an FcRn+/+ mouse versus an FcRn-/-, +huFcRn mouse. Quantitative PCR was performed (as in FIG. 3) from age- and gender-matched normal FcRn+/+ (S1, black bars) and FcRn-/-, +huFcRn Tg (S2, white bars) to determine the amount of FcRn mRNA in the examined tissues.

Development of a mouse model for SLE will allow testing of therapies directed against human FcRn. Therapeutics developed in the mouse model system, which utilizes human FcRn (huFcRn), will accelerate the transition to a clinical arena. To facilitate this process, transgenic mice will be produced which lack mouse FcRn but express huFcRn regulated in the appropriate manner. A number of Tg lines have been produced which carry a 33 kb human cosmid including the complete FcRn gene plus 10 kb 5' and 10 kb 3' flanking sequence. Non-quantitative PCR indicates that 5 of the lines express huFcRn transcript. Quantitative RT-PCR analysis of the huFcRn transgenic mouse indicates normal levels and fidelity of expression patterns of huFcRn compared with mouse FcRn (FIG. 6). To establish huFcRn protein expression, Western blot analysis using anti-huFcRn antiserum, described below, will be performed.

Figure 7:
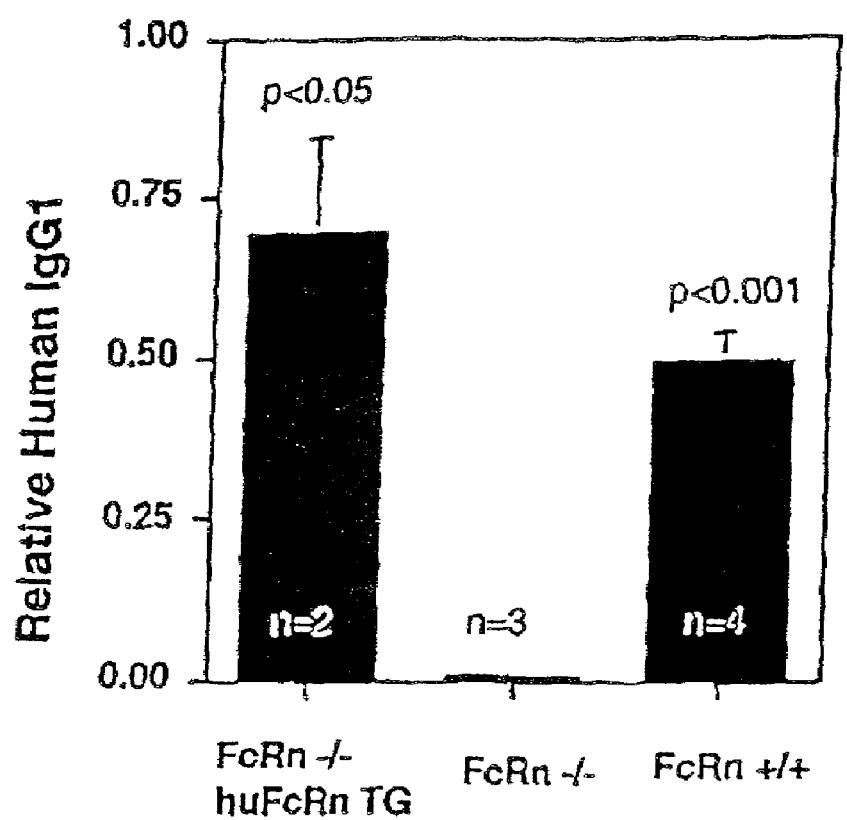
FIG. 7 is a bar graph indicating the presence of administered human IgG1 in the transgenic knockout mice. Data from transgenic line number 32 carrying the human genomic FcRn transgenic and then crossed to the FcRn-/- mouse is shown. Purified human IgG1 as a tracer was injected to the indicated mice. The serum concentration of the human IgG1 was then determined for the mice 8 days after injection. n is the indicated number of mice tested. Data shown are the mean+standard deviation of the concentration of tracer human IgG1 measured in day 1 serum samples divided by the concentration in serum samples from day 8 of the same individual mice. P values vs. FcRn-/- mice were computed using the one-sided Student's T Test.

To determine if the human FcRn transgenic was functioning in the mice, the ability of the huFcRn to protect human IgG1 from rapid clearance from the bloodstream was examined. muFcRn−/−, huFcRn mice, muFcRn−/− mice, and FcRn+/+ mice were given human IgG1 intravenously and followed for degradation of the administered human IgG1. As shown in FIG. 7, the human IgG1 was rapidly degraded in the FcRn−/− mice, as expected. As expected, the general level of protection conferred by mouse and human FcRn to IgG Abs will be roughly similar (Ghetie and Ward, Annu. Rev. Immunol. 18: 739–66 (2000); West and Bjorkman, Biochemistry 39: 9698–708 (2000)). The presence of the huFcRn transgene protected the human IgG1, to at least the same degree as the wild type FcRn.

The ability of the FcRn−/− mice expressing huFcRn to recapitulate the SLE characteristics found in wild-type mice will be verified experimentally. The huFcRn transgene will be transferred into SLE-predisposed mouse strains, MRL-FAS$^{lpr}$, NZM2410 strain backgrounds using speed congenic methods, to produce stocks of MRL-Fas$^{lpr}$ FcRn−−, huFcRn and NZM2410 FcRn−/−, huFcRn mice. These mice are also expected to develop the characteristics of SLE, and will be analyzed for such using the methods outlined above. The expected finding that MRL-Fas$^{lpr}$ FcRn−/− huFcRn Tg and NZM2410 FcRn−/−, huFcRn mice develop the same quality and quantity of SLE as wild-type controls, will indicate that huFcRn is functionally equivalent to mouse FcRn in terms of its ability to contribute to the SLE process. In the event that only some, but not all disease hallmarks are ameliorated, the mice will still provide a valuable vehicle to develop human FcRn based therapeutics.

Development of Assays to Screen for Molecules which Block Human FcRn

The information provided above relating to the role of FcRn in IgG protection and the development of SLE will be used to develop highly specific Abs and other drugs to counteract its contribution to pathogenesis in SLE and other FcRn related autoimmune diseases.

An ELISA for Detection of mABs which Specifically Bind HuFcRn/huβ2M

An in vitro assay for identifying molecules that block human FcRn function, in the form of a microtiter plate based assay, will be developed. The assay can be used to screen and identify molecules that bind human FcRn, such as anti-FcRn monoclonal Abs (mAbs) discussed below, as well as reengineered mAb derivatives and small molecules. Soluble huFcRn and huβ2M proteins will be expressed in pET-vector based bacterial expression systems.

Towards this end, a huFcRn cDNA lacking coding sequence for the membrane spanning region has been subcloned into pCR2.1. A huB2mpET construct has been obtained for expressing the light chain of functionally active class I MHC molecules. Properly folded huFcRn/huβ2M complexes will be purified using an human IgG1 affinity column, and analyzed by gel chromatography. Functional complexes are expected to bind IgG at pH 6 and be released at pH 7.2. Mammalian cell line expressed soluble huFcRn/huβ2M complexes will be used as an alternative method of production using established methods (reference JBC article and West et al., 39:9698–708). Supernatants will be purified by an IgG column as described above.

The purified huFcRn/huβ2M will be used to produce an ELISA assay for detection of mAbs that specifically bind huFcRn/huβ2M. ELISA microtiter plates will be coated with purified huFcRn/huβ2M complexes. The complexes will then be used to screen for anti-FcRn mAbs which bind to the complexes. Specific binding will be determined using horse radish peroxidase-conjugated F(ab')2 fragments specific for mouse IgG Fc fragments.

A competitive binding ELISA assay will be used to screen for molecules that prevent IgG from binding huFcRn/Huβ2M at pH 6. Candidate therapeutics must be able to prevent FcRn from binding IgG Abs in the acidic pH 6 endosomal environment. In this assay, functional huFcRn/huβ2M complexes will be bound to microtiter wells, and then used in an ELISA assay to determine the concentrations of human IgG1 that when added, bind and saturate huFcRn/huβ2M complexes at pH 6. Binding of human IgG1 will be revealed using an anti-human IgG1 horseradish peroxidase conjugated F(ab')2 fragment. Test anti-FcRn mAbs, will then be added to determine whether they competitively inhibit the binding of the human IgG1. Anti-FcRn Abs that are therapeutic candidates would be expected to efficiently inhibit the ability of the human IgG1 to bind FcRn. In addition, this assay will be used to identify other agents, such as small molecules, which block FcRn binding to IgG.

In vivo Assays for Identifying Inhibitors of FcRn

A cell culture assay will be developed to identify molecules that block human FcRn from protecting IgG in vivo. Cells in culture which are competent for catabolizing IgG efficiently, will be identified by screening existing cell lines (including COS, CHO, 3T3, 293, HUV-EC-C and SVEC) for the ability to catabolize serum proteins and non-IgG antibodies. This will be determined by adding low serum medium to the cells in culture, and determining the rate of clearance of added proteins from the medium. Once appropriate cell lines are identified, the cells will be tranfected with an expression construct (transient or stable) encoding huFcRn (or a control vector). Protein expression will be confirmed using anti-huFcRn mAbs. The transfected cells expressing huFcRn will be further analyzed for, whether they have a retarded rate of clearance of IgG due to huFcRn expression. This will indicate that the HuFcRn is functional in those cells. Cell lines identified as exhibiting a retarded rate of clearance of IgG will be used to identify molecules (e.g., monoclonal antibodies, small molecules, etc.), which prevent huFcRn from protecting IgG in vivo.

Screening of Potential Therapeutics in a Mouse Model

The ability of candidate therapeutics to decrease the half-life of tracer IgG, but not tracer IgA in a FcRn−/− huFcRn transgenic mouse, will be assayed. Therapeutics which are identified in this assay will be further analyzed for the ability to ameliorate SLE in FcRn−/− huFcRn Tg mouse models discussed above.

Generation of Monoclonal Antibodies Directed Against Human FcRn

High specificity anti-FcRn antisera have been difficult to produce. Rabbit anti-mouse and anti-human FcRn heteroantisera exist, but their specificity is problematic, and their use is generally restricted to Western and immunohistological analysis. This problem will be overcome through the generation of anti-FcRn mabs in the FcRn−/− mice. Because these mice develop in the absence of FcRn, the FcRn molecule as antigen will be recognized as foreign by the mouse immune system, resulting in the production of high affinity monoclonal antibodies to FcRn. Two basic immunization protocols will be employed. The first is to immunize FcRn−/− mice transgenic for the huβ2M transgene (thus carrying both mouse and human β2M) in the footpad with purified huFcRn/huβ2M complexes (produced as described above), admixed with complete Freund's adjuvant, and challenge 2× with the same material in incomplete adjuvant. The second approach is to deliver the same preparation ip, and boost 2× with teased liver cells from FcRn−/− huFcRn Tg mice. Sera collected from both mouse groups will be tested for specific activity using the above described ELISA assay, in which FcRn/huβ2M is bound to the microwells. Fusions will be carried out using conventional methods, and hybridoma clones will be screened using the Level 1 ELISA at pH 7. Supernatants from stable hybridomas demonstrating specific anti-huFcRn activity via ELISA will be further screened for their isotypes, and the hybridomas will be cryopreserved in microtiter wells. Among the hybridomas, those that serve one or more of several purposes, including high specific titer, sensitive detection of cell surface expression of FcRn via FACS, immunohistochemical staining of tissue sections, and crossreactivity to mouse FcRn (which would make the mAb applicable in all-mouse systems) will be selected. In addition, mAbs that retain specific binding at pH 6 via their antigen binding site rather than their Fc, will be identified. Such mAbs will be useful for in vivo therapies. These mabs should provide a valuable resource for a wide array of studies in both mice and humans.

Abs which specifically bind FcRn via their antigen binding site in a way that they sterically inhibit FcRn from binding IgG molecules via the Fc region, are expected to prevent the action of FcRn. Towards that end, the proposed ELISA screening assays will be used to identify mouse anti-human FcRn mAbs that bind huFcRn with high avidity, both at blood pH 7.2 and at the early endosomal pH 6 at which FcRn binds IgG. These mAbs should bind FcRn on the cell surface, potentially selectively enhancing their endosomal uptake. mAbs identified by this manner can then be assayed via the above described competitive binding ELISA, for their ability to inhibit IgG from binding FcRn, followed by the additional in vitro and cell culture assays described above, ultimately culminating in testing their therapeutic efficacy in ameliorating SLE in the mouse models. Successful therapeutics in the mouse models will be humanized for human clinical testing by replacement of their mouse IgG constant region with the human counterpart.

Monoclonal Abs with Engineered Fc

Elegant studies have been conducted that exploit phage display and site-specific mutagenesis techniques to alter the Fc region of mouse IgG to increase its half-life (Kim et al., Eur. J. Immunol. 29: 2819–25 (1999); Ghetie et al., Nat. Biotechnol. 15: 637–40 (1997)). The same general approach will be used to maximize human IgG Fc binding to FcRn, with the goal of tying up FcRn in the endosomes so that it cannot protect endogenous IgG.

Small Molecules that Bind and Inactivate FcRn

Small molecule FcRn-based therapeutics are a highly attractive approach for the treatment of disease because of their ease of synthesis and delivery. The in vitro and cell culture screening assays described above will be adapted to screen other agents such as small molecules for the ability to block huFcRn/hu2βM function.

Methods

Generation of the muFcRn deficient mice. MuFcRn−/− mice were produced by standard gene targeting technology (Capecchi, M. R., Trends Genet 5: 70–76 (1989); Koller et al., Proc Natl Acad Sci USA 86: 8932–8935 (1989)). To produce the targeting construct, genomic clones carrying overlapping segments of the genomic muFcRn gene were identified by screening Genome System's 129/SvJ-derived bacterial artificial chromosome library for hybridization with a fragment of the muFcRn cDNA. A 2.6 kb BamHI-BamHI genomic fragment consistent with the genomic muFcRn (GenBank accession # D37874) was subcloned from one such clone for the 5' targeting vector arm, and a 5.2 kb 3' ApaI-EcoRI genomic fragment was subcloned for the 3' vector arm. The core targeting vector was the pGT-N28 gene targeting vector from New England BioLabs, into which the above muFcRn genomic 5' and 3' arms were ligated. This resulted in a construct comprised of the 5' 2.6 kb muFcRn fragment, followed by a Neomycin resistance cassette which replaced 1,588 nucleotides of the native muFcRn gene, followed by a 5.2 kb 3' muFcRn fragment. A diagrammatic representation of vector construction is shown in FIG. 1. A homologous recombination of this vector with the native muFcRn gene is expected to be a 1,588 base pair deletion that includes 853 nucleotides immediately upstream from Exon 1, all of Exon 1, and Intron 1, and 207 base pairs of exon 2. Overall verification of final vector construct was confirmed by restriction fragment mapping and DNA sequencing.

The muFcRn construct was electroporated into embryonal stem cells derived from the 129/svj-derived ESV/J-1182 cell line. Cells surviving G418 selection were isolated, and their DNAs were screened for homologous recombination by Southern blot analysis using genomic probes that flanked the 5' and 3' genomic arms of the insert. Clone 573 demonstrated the restriction fragment length polymorphism expected for a homologous recombination event into the FcRn gene. Clone 573 cells were then injected into the inner cell mass of blastocysts derived from C57BL/6 mice, which were then implanted into pseudopregnant female mice. Chimeric progeny from the implanted mice were identified that transmitted the targeting cassette. Mice homozygous for the targeting cassette were then produced. The absence of the 1,588 nucleotide segment was confirmed by the polymerase chain reaction (PCR) analysis using oligonucleotide primers that lie within or flank the deletion site. A mouse stock (#573) carrying this targeted deletion was maintained by PCR-based genotyping using oligonucleotide primers that distinguish the wild-type and targeted allele. FIG. 2 illustrates the screening strategy used to identify proper targeting in the disruption of the FcRn gene.

Real-time quantitative PCR analysis of muFcRn transcription. The ABI Prism 7700 was used for real-time detection of PCR products generated from 15 ul triplicate reactions containing the equivalent of 0.5 ul cDNA in the presence of SYBR Green Master Mix (Applied Biosystems). Parallel reactions were used for GAPDH-normalization. Mean Ct's were calculated and the muFcRn expression levels were determined via the ddct method (Applied Biosystems User Bulletin #2), and expression levels are represented relative to skeletal muscle muFcRn expression. Quantity of amplified products of cDNA from the respective mice are reported. Data are the mean of PCR primers amplified a 94 bp fragment from cDNA spanning exons 3 and 4 of muFcRn, which is 3' of the knockout deletion. PCR specificity was verified via SYBR Green dissociation curve analysis.

Measuring absorption of maternal IgG by neonatal mice. A female muFcRn+/− mouse was mated to a male muFcRn−/− mouse. At 17 days of gestation, the pregnant female was injected iv with 500 ug IgG1 anti-TNP (1B7.11) tracer Ab. Sera from her two day old pups were assayed for anti-TNP Ab activity by ELISA (Christianson et al., J. Immunol. 159: 4781–92 (1997)). DNA from the pup livers was used to determine their genotypes by PCR using oligonucleotide priers designed to discriminate the wild-type from the targeted muFcRn gene. P values vs. FcRn−/− mice were computed using the one-sided Student's T Test.

IgG Clearance Assays. 100 ug of both mouse IgG1 mAb (1B7.11) anti-TNP and mouse IgA anti-TNP (mAb 2F.11.15) were injected ip into 7 week old FcRn−/− mice, FcRn+/− littermate controls, or age-matched C57BL/6-B2m−/− mice. FcRn−/−, n=5; FcRn+/−, n=5; B2m−/−, n=3. Sera from the indicated times was assayed for isotype-specific (IgA or IgG) anti-TNP activity by ELISA (Christianson et al., Jn Imunol. 159: 4781–4792 (1997)).

Determination of specific Ig isotypes in the transgenic mice. Groups of 5, approximately 6 week old, mice of the indicated genotypes were bled from the retroorbital plexus and serum was prepared Concentration in $\mu$g/ml of IgM, IgG1, IgG2a, and IgA antibodies were determined by ELISA (Christianson et al., J Immunol. 176: 4933–4939 (1996); Christianson et al., J Immunol. 159: 4781–4792 (1997)). P values were computed using the one-sided Student's T Test.

Generation of transgenic lines that carry a human cosmid containing complete human FcRn gene. To produce mice expressing huFcRn with high fidelity to its natural tissue expression pattern, transgenic mice carrying the complete huFcRn gene were produced. The human FcRn gene is approximately 11 kb (Gen Bank accession number AF220542). A human-derived bacterial artificial chromosome (BAC) library from Genome Systems, Inc., was screened for the huFcRn gene. A 34 kb XhoI fragment that contains the complete huFcRn gene was cloned from this BAC into a SuperCos vector. Southern blot analysis (see below) using an 800 bp human cDNA as a probe confirms this fact. Digestion with XhoI cuts the clone from the vector and further digestion with EcoRV yields only a 16 and a 18 kb hybridizing fragment, suggesting a single restriction site in the center of the 34 kb fragment. Both of these fragments hybridize a huFcRn cDNA probe, indicating that the approximately FcRn gene maps to the middle of the XhoI fragment. Therefore, there was a high likelihood that the complete gene including upstream (and downstream) regulatory sequences is carried in this cosmid clone. The purified huFcRn genomic insert was injected into zygotes from C57BL/6J and BXSB/MpJ female mice, and 5 genomic huFcRn transgenic lines were established that expressed the FcRn as determined by RT-PCR analysis. These transgenic stocks are currently being crossed onto the MRL/MpJ and NZM2410 strain backgrounds to additionally produce MRL/MpJ-huFcRn transgenic and NZM2410-huFcRn transgenic mice.

Generation of transgenic lines that express a huFcRn cDNA molecule driven by a high efficiency heterologous promoter. To produce mice expressing huFcRn expressed at high levels, and in an array of tissues, a 1.4 kb EcoI/EcoI cDNA fragment was cut out of a pREP9 plasmid obtained from Clark Anderson (Ohio State University) that carries a complete human huFcRn cDNA molecule. This fragment was subcloned into the pBS plasmid and cut out of pBS with KpnI and NotI, and cloned into pZERO. A cDNA-containing XhoI fragment was then cut out of pZERO and cloned into Vector E, which is a derivative of a vector described by Miyasaki et al., Gene 79: 269–277 (1989).

In Vector E, provided by William Sly from Washington University, upstream of the cDNA insertion site, lies a Beta Actin promoter with intron 1 which is 1.4 kb in length. Upstream of the promoter lies a 0.34 kb CMV enhancer. Immediately downstream of the cDNA insertion site lies a 0.73 kb rabbit beta-globin intron. Downstream of the rabbit intron lies a SV40 polyA region. The backbone of the vector is pBluescript KS (+). The total plasmid size without the insert is 5.8 kb and with the FcRn cDNA is 6.2 kb. A purified huFcRn cDNA-containing fragment was then cut out of pZERO with a KpnI/XhoI partial digest and injected into zygotes from C57BL/6J and BXSB/MpJ female mice. Six cDNA huFcRn transgenic lines were established on these 2 strain backgrounds that expressed huFcRn as determined by RT-PCR analysis. These transgenic stocks are currently being crossed onto the MRL/MpJ and NZM2410 strain backgrounds to additionally produce MRL/MpJ-huFcRn transgenic and NZM2410-huFcRn transgenic mice.

Production of muFcRn−/− huFcRn Tg mice. To produce muFcRn−/− +huFcRn Tg mice, muFcRn−/− were crossed to a huFcRn transgenic mice. Resulting F2 progeny were typed by PCR using oligonucleotide primers that distinguish the muFcRn wild-type (+) allele and the targeted muFcRn-allele gene, along with the huFcRn line transgene. MuFcRn−/−, muFcRn−/−, +huFcRn transgenic and muFcRn wild-type (+/+) mice were then identified.

Analysis of FcRn mRNA expression in tissues of wild type and FcRn−/−. +huFcRn mice. ABI Prism 7700 was used for real time quantitative PCR analysis (as described above) of cDNA prepared from an age- and gender-matched normal muFcRn+/+ mouse, and a muFcRn−/− huFcRn transgenic line mouse. PCR primers specific for muFcRn (S1) amplified a 94 bp fragment from cDNA spanning exons 3 and 4 of mouse FcRn. PCR primers specific for huFcRn (S2) yielded a 111 bp product; no amplification signal was detected from a control muFcRn+/+ mouse at 40 cycles. Data are the mean of three replicate determinations relative to the expression levels in skeletal muscle.

Determination of human IgG1 protection in transgenic knockout mice. Progeny of muFcRn−/− mice crossed to a huFcRn transgenic line 32 mouse were typed by PCR using oligonucleotide primers, which distinguish the muFcRn wild=type and targeted gene, and also the huFcRn line 32 transgene. FcRn−/−, FcRn−/−, huFcRn transgenic, and muFcRn+/+ (wild-type) were identified and injected at 6–8 weeks of age intraperitoneally with 50 _g of purified human IgG1 (Sigma Chemicals) used as a tracer. The mice were then bled via the retroorbital plexus on Days 1 and 8, and the serum concentration of human IgG1 was determined by ELISA. For the ELISA, diluted serum samples were captured on ELISA plates with mouse anti-human IgG1 mAb (Pharmingen), then detected with alkaline phosphatase conjugated mouse anti-human kappa mAb (Pharmingen).

Analysis of leukocyte spleen cell subsets in the transgenic knockout mice. Spleen cells from muFcRn−/− and muFcRn+/+, or muFcRn+/− (used interchangeably as wild-type) littermates were analyzed by multiparameter flow cytometry for cell surface expression of leukocyte markers using a Becton Dickinson FACScan. CD4+ T cells were visualized and enumerated using a combination of CY5-conjugated anti-CD4 monoclonal antibody (mAb)+FITC-conjugated anti-CD3e mAB. CD8+ T cells were visualized and enumerated using a combination of PE-conjugated anti-CD8a mAB+FITC conjugated anti-CD3e mAB. B220+ B cells were monitored by their ability to be stained by APC-conjugated anti-CD45R (B220), but not by the FITC-conjugated anti±-CD3e mAB. Granulocytes were monitored by their binding both APC-conjugated anti-CD11a (Mac1) and FITC-conjugated anti-Ly6 (Gr-1) Mabs. All mAbs were purchased from PharMingen Inc.

What is claimed is:

1. A method to identify or characterize an inhibitor of IgG protection by human FcRn (huFcRn) comprising:
    a) providing a first and a second transgenic mouse whose genome comprises a homozygous disruption in its endogenous FcRn gene, and whose genome further comprises a DNA sequence encoding a human FcRn operably linked to a regulatory sequence, wherein said homozygous disruption prevents the expression of a functional endogenous FcRn protein, and wherein the mouse expresses a functional human FcRn protein (a muFcRn−/−, +huFcRn transgenic mouse);
    b) administering intravenously or intraperitoneally tracer human IgG and tracer human IgA to the first and the second transgenic mouse;
    c) administering intravenously or intraperitoneally a candidate inhibitor to the first transgenic mouse; and
    d) determining the half-life of the tracer human IgG and the half-life of the tracer human IgA in the first transgenic mouse which has received the candidate inhibitor and in the second transgenic mouse which has not received the candidate inhibitor, with a decrease in the half-life of the tracer human IgG, but not the tracer human IgA, in the first transgenic mouse, as compared to the half life of the tracer human IgG and the tracer human IgA respectively in the second transgenic mouse, being an indication that the candidate inhibitor inhibits FcRn protection of IgG.

2. A method to identify or characterize a candidate agent for FcRn-mediated drug stabilization, comprising:
    a) providing a formulation comprising a candidate agent for FcRn-mediated drug stability attached to a trackable composition;
    b) administering intravenously or intraperitoneally the formulation to a muFcRn−/−, +huFcRn transgenic mouse, and also to a muFcRn−/− transgenic mouse; and
    c) assaying the half-life of the formulation in the bloodstream of the muFcRn−/−, +huFcRn transgenic mouse and in the bloodstream of the muFcRn−/− transgenic mouse, with a substantially longer half-life of the formulation in the bloodstream of the muFcRn−/−, +huFcRn transgenic mouse than in the bloodstream of the muFcRn−/− transgenic mousebeing an indication that the candidate agent promotes FcRn-mediated drug stabilization.

3. The method of claim 2 wherein the candidate agent is derived from an IgG Fc region.

4. The method of claim 2 wherein the candidate agent is derived from an IgG Fc region or fragment thereof, or other molecules which are structurally-similar or similar in sequence identity to the Fc-region of IgG.

5. The method of claim 2 wherein the candidate agent is structurally-similar or similar in sequence identity to the Fc-region of IgG, such that the binding affinity of the candidate agent to the FcRn protein is greater than the binding affinity of the Fc-region of IgG to the FcRn protein.

6. A method for determining the difference in pharmacokinetics of a drug conferred by an FcRn-mediated drug stability candidate agent linked to the drug, comprising:
    a) providing a first trackable formulation comprising a drug linked to a FcRn-mediated drug stability candidate agent, and a second trackable formulation comprising the drug without the FcRn-mediated drug stability candidate agent;
    b) administering intravenously or intraperitoneally the first formulation to a first muFcRn−/−, +huFcRn transgenic mouse, and the second formulation to a second muFcRn−/−, +huFcRn transgenic mouse;
    c) determining the half-lives of the first and the second formulation in the bloodstream of the first and the second muFcRn−/−, +huFcRn transgenic mouse respectively; and
    d) comparing the half-lives determined in step c) to one another, thereby determining the difference in half-lives conferred to the drug by the FcRn-mediated drug stability candidate agent.

7. The method of claim 6 wherein the candidate agent is derived from an IgG Fc region.

8. The method of claim 6 wherein the candidate agent is derived from an IgG Fc region or fragment thereof, or other molecules which are structurally-similar or similar in sequence identity to the Fc-region of IgG.

9. The method of claim 6 wherein the candidate agent is structurally-similar or similar in sequence identity to the Fc-region of IgG, such that the binding affinity of the candidate agent to the FcRn protein is greater than the binding affinity of the Fc-region of IgG to the FcRn protein.

10. A method to identify or characterize a candidate agent for FcRn-mediated drug stabilization, comprising:
    a) providing a formulation comprising a candidate agent for FcRn-mediated drug stability formulated with a trackable composition;
    b) administering intravenously or intraperitoneally the formulation to a muFcRn−/−, +huFcRn transgenic mouse, and also to a muFcRn−/− transgenic mouse; and
    c) assaying the half-life of the formulation in the bloodstream of the muFcRn−/−, +huFcRn transgenic mouse and the bloodstream of the muFcRn−/− transgenic mouse, with a substantially longer half-life of the formulation in the bloodstream of the muFcRn−/−, +huFcRn transgenic mouse than in the bloodstream of the muFcRn−/− transgenic mouse being an indication that the candidate agent promotes FcRn-mediated drug stabilization.

11. A method for determining the difference in pharmacokinetics of a drug conferred by an FcRn-mediated drug stability candidate agent linked to the drug, comprising:
    a) providing a first trackable formulation comprising a drug linked to a FcRn-mediated drug stability candidate agent, and a second trackable formulation comprising the drug without the FcRn-mediated drug stability candidate agent;

b) administering intravenously or intraperitoneally the first and the second formulation to a muFcRn−/−, +huFcRn transgenic mouse;

c) determining the half-lives of the first and the second formulation in the bloodstream of the muFcRn−/−, +huFcRn transgenic mouse; and e) comparing the half-lives determined in step c) to one another, thereby determining the difference in half-lives conferred to the drug by the FcRn-mediated drug stability candidate agent.

* * * * *

UNITED STATES PATENT AND TRADEMARK OFFICE
CERTIFICATE OF CORRECTION

PATENT NO. : 6,992,234 B2
APPLICATION NO. : 09/993322
DATED : January 31, 2006
INVENTOR(S) : Derry Charles Roopenian It is certified that error appears in the above-identified patent and that said Letters Patent is hereby corrected as shown below:

In Claim 2, Column 25, line 58, please correct mousebeing to read --mouse being--.

Signed and Sealed this

Twenty-fifth Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,992,234 B2
APPLICATION NO. : 09/993322
DATED : January 31, 2006
INVENTOR(S) : Derry Roopenian It is certified that error appears in the above-identified patent and that said Letters Patent is hereby corrected as shown below:

At column 1, line 16, please delete "NIHDR56597" and add --NIHDK56597--.

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,992,234 B2 | Page 1 of 1 |
| APPLICATION NO. | : 09/993322 | |
| DATED | : January 31, 2006 | |
| INVENTOR(S) | : Derry Roopenian | |

It is certified that error appears in the above-identified patent and that said Letters Patent is hereby corrected as shown below:

Government Support paragraph, at column 1, replace lines 15-18 with the following:

"This invention was made with government support under NIHDK56597 awarded by the National Institutes of Health. The government has certain rights in the invention."

Signed and Sealed this

Thirteenth Day of September, 2011

David J. Kappos
*Director of the United States Patent and Trademark Office*